(12) United States Patent
Escutia et al.

(10) Patent No.: US 11,045,125 B2
(45) Date of Patent: Jun. 29, 2021

(54) BODY FLUID SAMPLING DEVICE-SAMPLING SITE INTERFACE

(71) Applicant: Intuity Medical, Inc., Fremont, CA (US)

(72) Inventors: Raul Escutia, Sunnyvale, CA (US); Craig M. Litherland, San Jose, CA (US); Jeffrey L. Emery, Redwood City, CA (US); Jeffrey M. Jones, Sunnyvale, CA (US); Michael F. Tomasco, Morgan Hill, CA (US); Kelley J. Lipman, Livermore, CA (US)

(73) Assignee: Intuity Medical, Inc., Fremont, CA (US)

( * ) Notice: Subject to any disclaimer, the term of this patent is extended or adjusted under 35 U.S.C. 154(b) by 454 days.

(21) Appl. No.: 15/826,418

(22) Filed: Nov. 29, 2017

(65) Prior Publication Data
US 2018/0214059 A1     Aug. 2, 2018

Related U.S. Application Data

(63) Continuation of application No. 12/457,085, filed on Jun. 1, 2009, now Pat. No. 9,833,183.
(Continued)

(51) Int. Cl.
*A61B 5/15* (2006.01)
*A61B 5/151* (2006.01)
(Continued)

(52) U.S. Cl.
CPC ........ *A61B 5/150832* (2013.01); *A61B 5/157* (2013.01); *A61B 5/150022* (2013.01);
(Continued)

(58) Field of Classification Search
CPC ........ A61B 5/150832; A61B 5/150022; A61B 5/150068; A61B 5/150076;
(Continued)

(56) References Cited

U.S. PATENT DOCUMENTS

| 842,690 A | 1/1907 | Oswalt |
|---|---|---|
| D137,874 S | 5/1944 | Partidge |

(Continued)

FOREIGN PATENT DOCUMENTS

| CA | 2 201 530 A1 | 9/1997 |
|---|---|---|
| CA | 2 513 465 A1 | 8/2004 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.
(Continued)

*Primary Examiner* — Daniel L Cerioni
(74) *Attorney, Agent, or Firm* — Cooley LLP

(57) ABSTRACT

An arrangement for producing a sample of body fluid from a wound opening created in a skin surface at a sampling site includes: a housing, the housing comprising a first opening; a skin interface member disposed in the first opening, the skin interface member comprising an inner member having a second opening, and an outer member at least partially surrounding the inner member and attached to the first opening; and at least one skin-penetration member configured and arranged to project within the second opening. Arrangements having alternatively constructed skin interface members are also described.

25 Claims, 11 Drawing Sheets

Related U.S. Application Data

(60) Provisional application No. 61/129,025, filed on May 30, 2008.

(51) Int. Cl.
*A61B 5/157* (2006.01)
*A61M 5/42* (2006.01)

(52) U.S. Cl.
CPC .. *A61B 5/150068* (2013.01); *A61B 5/150076* (2013.01); *A61B 5/150083* (2013.01); *A61B 5/150091* (2013.01); *A61B 5/150099* (2013.01); *A61B 5/15107* (2013.01); *A61B 5/15109* (2013.01); *A61B 5/15117* (2013.01); *A61B 5/15151* (2013.01); *A61B 5/15161* (2013.01); *A61B 5/150183* (2013.01); *A61B 5/150229* (2013.01); *A61B 5/150259* (2013.01); *A61B 5/150267* (2013.01); *A61B 5/150274* (2013.01); *A61B 5/150389* (2013.01); *A61B 5/150412* (2013.01); *A61B 5/150809* (2013.01); *A61B 5/150816* (2013.01); *A61B 5/150824* (2013.01); *A61B 5/150954* (2013.01); *A61B 5/150984* (2013.01); *A61B 5/150442* (2013.01); *A61B 5/150748* (2013.01); *A61M 5/422* (2013.01)

(58) Field of Classification Search
CPC ........ A61B 5/150083; A61B 5/150091; A61B 5/150099; A61B 5/150183; A61B 5/150229; A61B 5/150259; A61B 5/150267; A61B 5/150274; A61B 5/150389; A61B 5/150412; A61B 5/150809; A61B 5/150816; A61B 5/150824; A61B 5/150954; A61B 5/150984; A61B 5/15107; A61B 5/15109; A61B 5/15117; A61B 5/15151; A61B 5/15161; A61B 5/157
USPC ........................................................ 600/584
See application file for complete search history.

(56) References Cited

U.S. PATENT DOCUMENTS

| | | | |
|---|---|---|---|
| 2,749,797 | A | 3/1950 | Harks |
| 3,092,465 | A | 6/1963 | Adams, Jr. |
| 3,310,002 | A | 3/1967 | Wilburn |
| 3,620,209 | A | 11/1971 | Kravitz |
| 3,623,475 | A | 11/1971 | Sanz et al. |
| 3,626,929 | A | 12/1971 | Sanz et al. |
| 3,630,957 | A | 12/1971 | Rey |
| D223,165 | S | 3/1972 | Komendat |
| 3,723,064 | A | 3/1973 | Liotta |
| 3,741,197 | A | 6/1973 | Sanz et al. |
| 3,961,898 | A | 6/1976 | Neeley et al. |
| 3,992,158 | A | 11/1976 | Przybylowicz et al. |
| 4,014,328 | A | 3/1977 | Cluff et al. |
| 4,042,335 | A | 8/1977 | Clement |
| 4,057,394 | A | 11/1977 | Genshaw |
| 4,109,655 | A | 8/1978 | Chacornac |
| 4,253,083 | A | 2/1981 | Imamura |
| 4,254,083 | A | 3/1981 | Columbus |
| 4,258,001 | A | 3/1981 | Pierce et al. |
| 4,260,257 | A | 4/1981 | Neeley et al. |
| 4,289,459 | A | 9/1981 | Neeley et al. |
| 4,321,397 | A | 3/1982 | Nix et al. |
| 4,350,762 | A | 9/1982 | DeLuca et al. |
| 4,394,512 | A | 7/1983 | Batz |
| 4,414,975 | A | 11/1983 | Ryder et al. |
| 4,416,279 | A | 11/1983 | Lindner et al. |
| 4,418,037 | A | 11/1983 | Katsuyama et al. |
| 4,422,941 | A | 12/1983 | Vaughan, Jr. et al. |
| 4,429,700 | A | 2/1984 | Thees et al. |
| 4,627,445 | A | 12/1986 | Garcia et al. |
| 4,637,403 | A | 1/1987 | Garcia et al. |
| 4,637,406 | A | 1/1987 | Guinn et al. |
| 4,653,513 | A | 3/1987 | Dombrowski |
| 4,661,319 | A | 4/1987 | Lape |
| 4,702,261 | A | 10/1987 | Cornell et al. |
| 4,711,250 | A | 12/1987 | Gilbaugh, Jr. et al. |
| 4,737,458 | A | 4/1988 | Batz et al. |
| 4,747,687 | A | 5/1988 | Hoppe et al. |
| 4,767,415 | A | 8/1988 | Duffy |
| 4,774,192 | A | 9/1988 | Terminiello et al. |
| 4,790,979 | A | 12/1988 | Terminiello et al. |
| 4,794,926 | A | 1/1989 | Munsch et al. |
| 4,815,843 | A | 3/1989 | Tiefenthaler et al. |
| 4,829,470 | A | 5/1989 | Wang |
| 4,844,095 | A | 7/1989 | Chiodo et al. |
| 4,846,785 | A | 7/1989 | Cassou et al. |
| 4,887,306 | A | 12/1989 | Hwang et al. |
| 4,920,977 | A | 5/1990 | Haynes |
| 4,929,426 | A | 5/1990 | Bodai et al. |
| 4,930,525 | A | 6/1990 | Palestrant |
| 4,935,346 | A | 6/1990 | Phillips |
| 4,953,552 | A | 9/1990 | De Marzo |
| 4,966,646 | A | 10/1990 | Zdeblick |
| 4,983,178 | A | 1/1991 | Schnell |
| 4,995,402 | A | 2/1991 | Smith |
| 5,026,388 | A | 6/1991 | Ingalz |
| 5,029,583 | A | 7/1991 | Meserol |
| 5,035,704 | A | 7/1991 | Lambert et al. |
| 5,037,199 | A | 8/1991 | Hlousek |
| 5,049,487 | A | 9/1991 | Phillips et al. |
| 5,050,617 | A | 9/1991 | Columbus et al. |
| 5,054,878 | A | 10/1991 | Gergely et al. |
| 5,059,394 | A | 10/1991 | Phillips et al. |
| 5,077,199 | A | 12/1991 | Basagni et al. |
| 5,094,943 | A | 3/1992 | Siedel et al. |
| 5,110,724 | A | 5/1992 | Hewett |
| 5,114,350 | A | 5/1992 | Hewett |
| 5,116,759 | A | 5/1992 | Klainer et al. |
| 5,131,404 | A | 7/1992 | Neeley et al. |
| 5,141,868 | A | 8/1992 | Shanks et al. |
| 5,145,565 | A | 9/1992 | Kater et al. |
| 5,146,437 | A | 9/1992 | Boucheron |
| 5,153,416 | A | 10/1992 | Neeley |
| 5,164,575 | A | 11/1992 | Neeley et al. |
| 5,166,498 | A | 11/1992 | Neeley |
| 5,174,291 | A | 12/1992 | Schoonen et al. |
| 5,176,632 | A | 1/1993 | Bernardi |
| 5,179,005 | A | 1/1993 | Phillips et al. |
| 5,183,741 | A | 2/1993 | Arai et al. |
| 5,194,393 | A | 3/1993 | Hugl et al. |
| 5,196,302 | A | 3/1993 | Kidwell |
| 5,208,163 | A | 5/1993 | Charlton et al. |
| 5,213,966 | A | 5/1993 | Vuorinen et al. |
| 5,217,480 | A | 6/1993 | Habar et al. |
| 5,218,966 | A | 6/1993 | Yamasawa |
| 5,223,219 | A | 6/1993 | Subramanian et al. |
| 5,228,972 | A | 7/1993 | Osaka et al. |
| 5,234,818 | A | 8/1993 | Zimmermann et al. |
| 5,241,969 | A | 9/1993 | Carson et al. |
| 5,251,126 | A | 10/1993 | Kahn et al. |
| D341,848 | S | 11/1993 | Bigelow et al. |
| 5,269,800 | A | 12/1993 | Davis, Jr. |
| 5,275,159 | A | 1/1994 | Griebel |
| 5,278,079 | A | 1/1994 | Gubinski et al. |
| 5,279,294 | A | 1/1994 | Anderson et al. |
| 5,288,646 | A | 2/1994 | Lundsgaard et al. |
| 5,299,571 | A | 4/1994 | Mastrototaro |
| 5,301,686 | A | 4/1994 | Newman |
| 5,302,513 | A | 4/1994 | Mike et al. |
| 5,304,468 | A | 4/1994 | Phillips et al. |
| 5,306,623 | A | 4/1994 | Kiser et al. |
| 5,308,767 | A | 5/1994 | Terashima |
| 5,314,441 | A | 5/1994 | Cusack et al. |
| 5,320,607 | A | 6/1994 | Ishibashi |
| 5,354,537 | A | 10/1994 | Moreno |
| 5,360,595 | A | 11/1994 | Bell et al. |
| 5,368,047 | A | 11/1994 | Suzuki et al. |

(56) References Cited

U.S. PATENT DOCUMENTS

| | | |
|---|---|---|
| 5,383,512 A | 1/1995 | Jarvis |
| 5,390,671 A | 2/1995 | Lord et al. |
| 5,395,388 A | 3/1995 | Schraga |
| 5,399,316 A | 3/1995 | Yamada |
| 5,401,110 A | 3/1995 | Neeley |
| 5,402,798 A | 4/1995 | Swierczek et al. |
| 5,426,032 A | 6/1995 | Phillips et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,489,414 A | 2/1996 | Schreiber et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,518,689 A | 5/1996 | Dosmann et al. |
| 5,525,518 A | 6/1996 | Lundsgaard et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,578,014 A | 11/1996 | Erez et al. |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,602,647 A | 2/1997 | Xu et al. |
| 5,611,809 A | 3/1997 | Marshall et al. |
| 5,611,999 A | 3/1997 | Dosmann et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,638,828 A | 6/1997 | Lauks et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,700,695 A | 12/1997 | Yassinzadeh et al. |
| 5,701,181 A | 12/1997 | Boiarski et al. |
| 5,701,910 A | 12/1997 | Powles et al. |
| D389,761 S | 1/1998 | Thomas |
| 5,705,018 A | 1/1998 | Hartley |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,753,452 A | 5/1998 | Smith |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,789,255 A | 8/1998 | Yu |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,866,349 A | 2/1999 | Lilja et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,926,271 A | 7/1999 | Couderc et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,015,969 A | 1/2000 | Nathel et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,121,050 A | 9/2000 | Han |
| 6,123,861 A | 9/2000 | Santini, Jr. et al. |

(56) References Cited

U.S. PATENT DOCUMENTS

| | | |
|---|---|---|
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,184,990 B1 | 2/2001 | Amirkhanian et al. |
| 6,187,210 B1 | 2/2001 | Lebouiz et al. |
| 6,192,891 B1 | 2/2001 | Gravel et al. |
| 6,193,873 B1 | 2/2001 | Ohara et al. |
| 6,197,257 B1 | 3/2001 | Raskas |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,246,966 B1 | 6/2001 | Perry |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,812 B1 | 11/2001 | Sherman et al. |
| 6,312,888 B1 | 11/2001 | Wong et al. |
| 6,315,738 B1 | 11/2001 | Nishikawa et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,459,917 B1 * | 10/2002 | Gowda ............... A61B 5/14528 600/345 |
| 6,493,069 B1 | 12/2002 | Nagashimada et al. |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,193 B2 | 4/2003 | Abreu |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,571,114 B1 | 5/2003 | Koike et al. |
| 6,579,690 B1 | 6/2003 | Bonnecaze et al. |
| 6,589,260 B1 | 7/2003 | Schmelzeisen-Redeker et al. |
| 6,591,124 B2 | 7/2003 | Sherman et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,662,031 B1 | 12/2003 | Khalil et al. |
| 6,679,852 B1 | 1/2004 | Schmelzeisen-Redeker et al. |
| 6,690,467 B1 | 2/2004 | Reel |
| 6,706,000 B2 | 3/2004 | Perez et al. |
| 6,706,049 B2 | 3/2004 | Moerman |
| 6,706,159 B2 | 3/2004 | Moerman et al. |
| 6,707,554 B1 | 3/2004 | Miltner et al. |
| 6,740,800 B1 | 5/2004 | Cunningham |
| 6,743,635 B2 | 6/2004 | Neel et al. |
| 6,744,502 B2 | 6/2004 | Hoff et al. |
| 6,748,275 B2 | 6/2004 | Lattner et al. |
| 6,753,187 B2 | 6/2004 | Cizdziel et al. |
| 6,766,817 B2 | 7/2004 | da Silva |
| 6,775,001 B2 | 8/2004 | Friberg et al. |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,890,421 B2 | 5/2005 | Ohara et al. |
| 6,896,850 B2 | 5/2005 | Subramanian et al. |
| 6,903,815 B2 | 6/2005 | Uchiyama et al. |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| D511,214 S | 11/2005 | Sasano et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,154,592 B2 | 12/2006 | Reynolds et al. |
| 7,156,809 B2 | 1/2007 | Quy |
| 7,163,616 B2 | 1/2007 | Vreeke et al. |
| 7,183,552 B2 | 2/2007 | Russell |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| 7,229,458 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,316,700 B2 | 1/2008 | Alden et al. |
| 7,323,141 B2 | 1/2008 | Kirchhevel et al. |
| 7,323,315 B2 | 1/2008 | Marfurt |
| 7,341,830 B2 | 3/2008 | Horn et al. |
| 7,343,188 B2 | 3/2008 | Sohrab |
| 7,344,507 B2 | 3/2008 | Briggs et al. |
| 7,377,904 B2 | 5/2008 | Conway et al. |
| 7,379,167 B2 | 5/2008 | Mawhirt et al. |
| 7,427,377 B2 | 9/2008 | Zanzucchi et al. |
| 7,439,033 B2 | 10/2008 | Marfurt |
| D580,068 S | 11/2008 | Shigesada et al. |
| D580,558 S | 11/2008 | Shigesada et al. |

(56) References Cited

U.S. PATENT DOCUMENTS

| | | |
|---|---|---|
| 7,501,053 B2 | 3/2009 | Karinka et al. |
| 7,537,571 B2 | 5/2009 | Freeman et al. |
| D599,373 S | 9/2009 | Kobayashi et al. |
| D601,257 S | 9/2009 | Berlinger |
| 7,582,063 B2 | 9/2009 | Wurster et al. |
| 7,585,278 B2 | 9/2009 | Aceti et al. |
| D601,444 S | 10/2009 | Jones et al. |
| D601,578 S | 10/2009 | Poulet et al. |
| 7,655,019 B2 | 2/2010 | LeVaughn et al. |
| 7,682,318 B2 | 3/2010 | Alden et al. |
| 7,713,214 B2 | 5/2010 | Freeman et al. |
| 7,725,149 B2 | 5/2010 | Peyser et al. |
| D622,393 S | 8/2010 | Gatrall et al. |
| 7,780,610 B2 | 8/2010 | Sonoda et al. |
| 7,780,631 B2 | 8/2010 | Lum et al. |
| 7,803,123 B2 | 9/2010 | Perez et al. |
| 7,819,822 B2 | 10/2010 | Calasso et al. |
| 7,841,992 B2 | 11/2010 | Freeman et al. |
| 7,879,058 B2 | 2/2011 | Ikeda |
| 7,883,473 B2 | 2/2011 | LeVaughn et al. |
| 7,887,494 B2 | 2/2011 | Emery et al. |
| 7,955,492 B2 | 6/2011 | Fujiwara et al. |
| 7,964,372 B2 | 6/2011 | Marfurt |
| D642,191 S | 7/2011 | Barnett et al. |
| 7,972,861 B2 | 7/2011 | Deng et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 | 1/2012 | McDevitt et al. |
| D654,926 S | 2/2012 | Lipman et al. |
| 8,173,439 B2 | 5/2012 | Petrich |
| 8,184,273 B2 | 5/2012 | Dosmann et al. |
| 8,202,231 B2 | 6/2012 | Freeman et al. |
| 8,231,832 B2 | 7/2012 | Zanzucchi et al. |
| 8,251,920 B2 | 8/2012 | Vreeke et al. |
| 8,262,614 B2 | 9/2012 | Freeman et al. |
| 8,267,870 B2 | 9/2012 | Freeman et al. |
| 8,280,476 B2 | 10/2012 | Jina |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,372,016 B2 | 2/2013 | Freeman et al. |
| 8,376,959 B2 | 2/2013 | Deck |
| 8,382,681 B2 | 2/2013 | Escutia et al. |
| 8,391,940 B2 | 3/2013 | Matzinger et al. |
| 8,419,657 B2 | 4/2013 | Roe |
| D691,174 S | 10/2013 | Lipman et al. |
| 8,574,168 B2 | 11/2013 | Freeman et al. |
| 8,574,895 B2 | 11/2013 | Freeman et al. |
| 8,696,880 B2 | 4/2014 | Beer et al. |
| 8,702,624 B2 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,017,356 B2 | 4/2015 | Schraga et al. |
| 9,034,639 B2 | 5/2015 | Freeman et al. |
| 9,060,723 B2 | 6/2015 | Escutia et al. |
| 9,060,727 B2 | 6/2015 | Saikley et al. |
| 9,063,102 B2 | 6/2015 | Hoenes et al. |
| 9,089,678 B2 | 7/2015 | Freeman et al. |
| 9,095,292 B2 | 8/2015 | Zanzucchi et al. |
| 9,095,847 B2 | 8/2015 | Porsch et al. |
| 9,097,679 B2 | 8/2015 | List et al. |
| 9,101,302 B2 | 8/2015 | Mace et al. |
| 9,131,886 B2 | 9/2015 | Harttig et al. |
| 9,138,179 B2 | 9/2015 | Hoenes et al. |
| 9,149,215 B2 | 10/2015 | Werner et al. |
| 9,173,608 B2 | 11/2015 | Kuhr et al. |
| 9,179,872 B2 | 11/2015 | Roe et al. |
| 9,186,097 B2 | 11/2015 | Frey et al. |
| 9,186,104 B2 | 11/2015 | Kraemer et al. |
| 9,186,468 B2 | 11/2015 | Freeman et al. |
| 9,226,704 B2 | 1/2016 | Deck |
| 9,301,171 B2 | 4/2016 | List et al. |
| 9,314,194 B2 | 4/2016 | Deshmukh et al. |
| 9,326,718 B2 | 5/2016 | Petrich et al. |
| 9,332,931 B2 | 5/2016 | Chan |
| 9,332,932 B2 | 5/2016 | Okuyama et al. |
| 9,339,612 B2 | 5/2016 | Freeman et al. |
| 9,351,680 B2 | 5/2016 | Boecker et al. |
| 9,364,172 B2 | 6/2016 | Konya et al. |
| 9,366,636 B2 | 6/2016 | Emery et al. |
| 9,375,169 B2 | 6/2016 | Choi et al. |
| 9,375,177 B2 | 6/2016 | Planman et al. |
| 9,380,963 B2 | 7/2016 | Gofman et al. |
| 9,380,974 B2 | 7/2016 | Emery et al. |
| 9,386,944 B2 | 7/2016 | Freeman et al. |
| 9,392,968 B2 | 7/2016 | Schraga |
| 9,439,591 B2 | 9/2016 | Frey et al. |
| 9,463,463 B2 | 10/2016 | He et al. |
| 9,480,419 B2 | 11/2016 | Weiss et al. |
| 9,480,420 B2 | 11/2016 | Konya et al. |
| 9,486,164 B2 | 11/2016 | Roe |
| 9,488,585 B2 | 11/2016 | Emeric et al. |
| 9,517,027 B2 | 12/2016 | Kan et al. |
| 9,560,993 B2 | 2/2017 | Freeman |
| 9,561,000 B2 | 2/2017 | Lum |
| 9,573,761 B2 | 2/2017 | List |
| 9,599,552 B2 | 3/2017 | Baldus et al. |
| 9,603,562 B2 | 3/2017 | Aceti et al. |
| 9,636,051 B2 | 5/2017 | Emery et al. |
| 9,668,687 B2 | 6/2017 | Volkmuth et al. |
| 9,671,387 B2 | 6/2017 | Thoes et al. |
| 9,717,452 B2 | 8/2017 | Roe et al. |
| 9,724,021 B2 | 8/2017 | Freeman et al. |
| 9,730,625 B2 | 8/2017 | Krasnow et al. |
| 9,782,114 B2 | 10/2017 | Reynolds et al. |
| 9,795,334 B2 | 10/2017 | Freeman et al. |
| 9,820,684 B2 | 11/2017 | Freeman et al. |
| 9,833,183 B2 | 12/2017 | Escutia et al. |
| 9,839,384 B2 | 12/2017 | Escutia et al. |
| 9,877,676 B2 | 1/2018 | Konya et al. |
| 9,880,254 B2 | 1/2018 | Richter et al. |
| 9,883,828 B2 | 2/2018 | Haar et al. |
| 9,897,610 B2 | 2/2018 | Lipman et al. |
| 9,927,386 B2 | 3/2018 | Wang et al. |
| 9,931,478 B2 | 4/2018 | Hirshberg et al. |
| 9,939,403 B2 | 4/2018 | Richter et al. |
| 9,939,404 B2 | 4/2018 | Richter et al. |
| 9,943,256 B2 | 4/2018 | Varsavsky et al. |
| 9,943,259 B2 | 4/2018 | Kuhr et al. |
| 9,949,679 B2 | 4/2018 | Renlund |
| 9,965,587 B2 | 5/2018 | Aykroyd et al. |
| 9,968,284 B2 | 5/2018 | Vidalis et al. |
| 9,974,471 B1 | 5/2018 | Kam et al. |
| 9,983,140 B2 | 5/2018 | Dickopf |
| 9,987,427 B1 | 6/2018 | Polsky et al. |
| 10,034,628 B2 | 7/2018 | Freeman et al. |
| 10,080,517 B2 | 9/2018 | Chen et al. |
| 10,194,838 B2 | 2/2019 | Weiss et al. |
| 10,226,208 B2 | 3/2019 | Emery et al. |
| 10,278,621 B2 | 5/2019 | List |
| 10,309,905 B2 | 6/2019 | Dickopf |
| 10,327,689 B2 | 6/2019 | Krasnow et al. |
| 10,330,667 B2 | 6/2019 | Lipman et al. |
| 10,383,556 B2 | 8/2019 | Lipman et al. |
| 10,429,337 B2 | 10/2019 | Malecha et al. |
| 10,433,780 B2 | 10/2019 | Escutia et al. |
| 10,441,205 B2 | 10/2019 | Litherland et al. |
| 10,729,386 B2 | 8/2020 | Lipman et al. |
| 10,772,550 B2 | 9/2020 | Aceti et al. |
| 10,842,427 B2 | 11/2020 | Escutia et al. |
| 2001/0001034 A1 | 5/2001 | Douglas |
| 2001/0027277 A1 | 10/2001 | Klitmose |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |

(56) References Cited

U.S. PATENT DOCUMENTS

| | | |
|---|---|---|
| 2002/0020688 A1 | 2/2002 | Sherman et al. |
| 2002/0022934 A1 | 2/2002 | Vogel et al. |
| 2002/0023852 A1 | 2/2002 | Mcivor et al. |
| 2002/0042594 A1 | 4/2002 | Lum et al. |
| 2002/0045243 A1 | 4/2002 | Laska et al. |
| 2002/0052618 A1 | 5/2002 | Haar et al. |
| 2002/0067481 A1 | 6/2002 | Wolf et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0188224 A1 | 12/2002 | Roe et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0143746 A1 | 7/2003 | Sage |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0187395 A1 | 10/2003 | Gabel et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-redeker et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0120848 A1 | 6/2004 | Teodorczyk |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | Levaughn et al. |
| 2004/0232180 A1 | 11/2004 | Badillo |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0015020 A1 | 1/2005 | LeVaughn et al. |
| 2005/0027182 A1 | 2/2005 | Siddiqui et al. |
| 2005/0033340 A1 | 2/2005 | Lipoma et al. |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0153428 A1 | 7/2005 | Matsumoto |
| 2005/0154410 A1 | 7/2005 | Conway et al. |
| 2005/0159678 A1 | 7/2005 | Taniike et al. |
| 2005/0176133 A1 | 8/2005 | Miyashita et al. |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage, Jr. et al. |
| 2005/0215872 A1 | 9/2005 | Berner et al. |
| 2005/0215923 A1 | 9/2005 | Wiegel |
| 2005/0234486 A1 | 10/2005 | Allen et al. |
| 2005/0234494 A1 | 10/2005 | Conway et al. |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0184189 A1 | 8/2006 | Olson et al. |
| 2006/0189908 A1 | 8/2006 | Kennedy |
| 2006/0200044 A1 | 9/2006 | Freeman et al. |
| 2006/0204399 A1 | 9/2006 | Freeman et al. |
| 2006/0224172 A1 | 10/2006 | LeVaughn et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0264996 A1 | 11/2006 | LeVaughn et al. |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0060842 A1 | 3/2007 | Alvarez-Icaza et al. |
| 2007/0078313 A1 | 4/2007 | Emery et al. |
| 2007/0078358 A1 | 4/2007 | Escutia et al. |
| 2007/0083130 A1 | 4/2007 | Thomson et al. |
| 2007/0083131 A1 | 4/2007 | Escutia et al. |
| 2007/0100255 A1 | 5/2007 | Boecker et al. |
| 2007/0112281 A1 | 5/2007 | Olson |
| 2007/0179404 A1 | 8/2007 | Escutia et al. |
| 2007/0179405 A1 | 8/2007 | Emery et al. |
| 2007/0208309 A1* | 9/2007 | Flora ............... A61B 5/150068 604/140 |
| 2007/0253531 A1 | 11/2007 | Okuzawa et al. |
| 2007/0255181 A1 | 11/2007 | Alvarez-icaza et al. |
| 2007/0255302 A1 | 11/2007 | Koeppel et al. |
| 2008/0046831 A1 | 2/2008 | Imai et al. |
| 2008/0077048 A1 | 3/2008 | Escutia et al. |
| 2008/0139910 A1 | 6/2008 | Mastrototaro et al. |
| 2008/0194934 A1 | 8/2008 | Ray et al. |
| 2008/0255598 A1 | 10/2008 | LeVaughn et al. |
| 2008/0269625 A1 | 10/2008 | Halperin et al. |
| 2008/0274447 A1 | 11/2008 | Mecklenburg |
| 2009/0054810 A1 | 2/2009 | Zanzucchi et al. |
| 2009/0099437 A1 | 4/2009 | Yuzhakov |
| 2009/0156923 A1 | 6/2009 | Power et al. |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1 | 1/2010 | Lipman et al. |
| 2010/0095229 A1 | 4/2010 | Dixon et al. |
| 2010/0152660 A1 | 6/2010 | Mack et al. |
| 2010/0174211 A1 | 7/2010 | Frey et al. |

(56) References Cited

U.S. PATENT DOCUMENTS

| | | |
|---|---|---|
| 2010/0185120 A1 | 7/2010 | Sacherer et al. |
| 2010/0217155 A1 | 8/2010 | Poux et al. |
| 2010/0249652 A1 | 9/2010 | Rush et al. |
| 2010/0331650 A1 | 12/2010 | Batman et al. |
| 2011/0098599 A1 | 4/2011 | Emery et al. |
| 2011/0105872 A1 | 5/2011 | Chickering, III et al. |
| 2011/0201909 A1 | 8/2011 | Emery et al. |
| 2011/0294152 A1 | 12/2011 | Lipman et al. |
| 2012/0166090 A1 | 6/2012 | Lipman et al. |
| 2012/0296179 A1 | 11/2012 | Zanzucchi et al. |
| 2013/0110516 A1 | 5/2013 | Abulhaj et al. |
| 2013/0158430 A1 | 6/2013 | Aceti et al. |
| 2013/0158432 A1 | 6/2013 | Escutia et al. |
| 2013/0172698 A1 | 7/2013 | Reynolds et al. |
| 2013/0274568 A1 | 10/2013 | Escutia et al. |
| 2013/0274579 A1 | 10/2013 | Richter et al. |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |
| 2015/0153351 A1 | 6/2015 | Lipman et al. |
| 2015/0182157 A1 | 7/2015 | Boriah et al. |
| 2015/0212006 A1 | 7/2015 | Emery et al. |
| 2015/0268228 A1 | 9/2015 | Schulat et al. |
| 2015/0335272 A1 | 11/2015 | Natale et al. |
| 2016/0011178 A1 | 1/2016 | Hoenes et al. |
| 2016/0038066 A1 | 2/2016 | Escutia et al. |
| 2016/0256106 A1 | 9/2016 | Krasnow et al. |
| 2016/0367178 A1 | 12/2016 | Emery et al. |
| 2016/0374603 A1 | 12/2016 | Shaanan et al. |
| 2017/0095188 A1 | 4/2017 | Emery et al. |
| 2017/0319121 A1 | 11/2017 | Aceti et al. |
| 2017/0354355 A1 | 12/2017 | Emery et al. |
| 2018/0008178 A1 | 1/2018 | Escutia et al. |
| 2018/0296143 A1 | 10/2018 | Anderson et al. |
| 2018/0310865 A1 | 11/2018 | Escutia et al. |
| 2018/0338713 A1 | 11/2018 | Polsky et al. |
| 2019/0000365 A1 | 1/2019 | Beyerlein et al. |
| 2019/0025318 A1 | 1/2019 | Lipman et al. |
| 2019/0104976 A1 | 4/2019 | Reynolds et al. |
| 2019/0175086 A1 | 6/2019 | Yang |
| 2019/0209064 A1 | 7/2019 | Emery et al. |
| 2019/0209820 A1 | 7/2019 | Chickering, III et al. |
| 2019/0269358 A1 | 9/2019 | Messerschmidt |
| 2019/0274607 A1 | 9/2019 | Krasnow et al. |
| 2019/0391129 A1 | 12/2019 | Lipman et al. |
| 2020/0214605 A1 | 7/2020 | Lipman et al. |
| 2020/0237280 A1 | 7/2020 | Escutia et al. |

FOREIGN PATENT DOCUMENTS

| | | | |
|---|---|---|---|
| DE | 197 05 091 A1 | 2/1999 | |
| DE | 199 22 413 A1 | 11/2000 | |
| DE | 103 02-501 A1 | 8/2004 | |
| EP | 0 103 426 A2 | 3/1984 | |
| EP | 0 256 806 A2 | 2/1988 | |
| EP | 0 160 708 B1 | 10/1989 | |
| EP | 0 356 418 A2 | 2/1990 | |
| EP | 0 396-016 A2 | 11/1990 | |
| EP | 0 396-016 A3 | 11/1990 | |
| EP | 0 397 424 A2 | 11/1990 | |
| EP | 0 409 032 A2 | 1/1991 | |
| EP | 0 255-338 A2 | 2/1998 | |
| EP | 0 849 584 A2 | 6/1998 | |
| EP | 0 877 250 A2 | 11/1998 | |
| EP | 1 037 048 A2 | 9/2000 | |
| EP | 1 060 768 A2 | 12/2000 | |
| EP | 1 118 856 A1 | 7/2001 | |
| EP | 1 266-607 A2 | 12/2002 | |
| EP | 1 266-607 A3 | 12/2002 | |
| EP | 1 369 688 A2 | 10/2003 | |
| EP | 1 369 688 A3 | 10/2003 | |
| EP | 1 360-934 A1 | 11/2003 | |
| EP | 1 360-934 B1 | 11/2003 | |
| EP | 1 486-766 A1 | 12/2004 | |
| EP | 1 486-766 B1 | 12/2004 | |
| EP | 1 529-489 A1 | 5/2005 | |
| EP | 1 529-489 B1 | 5/2005 | |
| EP | 1 586-270 A2 | 10/2005 | |
| EP | 1 586-270 A3 | 10/2005 | |
| EP | 1 769-735 A1 | 4/2007 | |
| JP | 61-290342 A | 12/1986 | |
| JP | 63-305841 A | 12/1988 | |
| JP | 1-318963 A | 12/1989 | |
| JP | 3-63570 A | 3/1991 | |
| JP | 03093189 A | 4/1991 | |
| JP | 7-67861 A | 3/1995 | |
| JP | 7-213925 A | 8/1995 | |
| JP | 09-084781 A | 3/1997 | |
| JP | 9-168530 A | 6/1997 | |
| JP | 9-313465 A | 9/1997 | |
| JP | 9-266889 A | 10/1997 | |
| JP | 9-294737 A | 11/1997 | |
| JP | 10-024028 A | 1/1998 | |
| JP | 10-505258 A | 5/1998 | |
| JP | 10-508518 A | 8/1998 | |
| JP | 10-318970 A | 12/1998 | |
| JP | 63-305841 A2 | 12/1998 | |
| JP | 11-056822 A | 3/1999 | |
| JP | 11-281779 A | 10/1999 | |
| JP | 2000-126161 A | 5/2000 | |
| JP | 2000-168754 A | 6/2000 | |
| JP | 2000-254111 A | 9/2000 | |
| JP | 2001-017404 A | 1/2001 | |
| JP | 2001-159618 A | 6/2001 | |
| JP | 2001-515203 A | 9/2001 | |
| JP | 2001-281242 A | 10/2001 | |
| JP | 2001-305096 A | 10/2001 | |
| JP | 2001-309905 A | 11/2001 | |
| JP | 2001-330581 A | 11/2001 | |
| JP | 2002-000588 A | 1/2002 | |
| JP | 2002-502045 A | 1/2002 | |
| JP | 2002-085384 A | 3/2002 | |
| JP | 2002-514453 A | 5/2002 | |
| JP | 2002-219155 A | 8/2002 | |
| JP | 2003-507719 A | 2/2003 | |
| JP | 2003-108679 A | 4/2003 | |
| JP | 2003-180417 A | 7/2003 | |
| JP | 2004-000598 A | 1/2004 | |
| JP | 2004-500948 A | 1/2004 | |
| JP | 2004-117339 A | 4/2004 | |
| JP | 2004-202256 | 7/2004 | |
| JP | 2004-208727 A | 7/2004 | |
| JP | 2004-209266 A | 7/2004 | |
| JP | 2004-519302 A | 7/2004 | |
| JP | 2004-522500 A | 7/2004 | |
| JP | 2004-528936 A | 9/2004 | |
| JP | 2005-009238 A | 1/2005 | |
| JP | 3638958 B2 | 1/2005 | |
| JP | 2005-503538 A | 2/2005 | |
| JP | 2005-087613 A | 4/2005 | |
| JP | 2006-512969 A | 4/2005 | |
| JP | 2005-523065 A | 8/2005 | |
| JP | 2005-525149 A | 8/2005 | |
| JP | 2005-237938 A | 9/2005 | |
| JP | 2005-525846 A | 9/2005 | |
| JP | 2005-527254 A | 9/2005 | |
| JP | 2005-305157 A | 11/2005 | |
| JP | 2005-305159 A | 11/2005 | |
| JP | 2006-506185 A | 2/2006 | |
| JP | 2006-512974 A | 4/2006 | |
| JP | 2006-516723 A | 7/2006 | |
| JP | 2006-521555 A | 9/2006 | |
| JP | 2006-527013 A | 11/2006 | |
| JP | 2007-014381 A | 1/2007 | |
| JP | 2007-054407 A | 3/2007 | |
| JP | 2007-136198 A | 6/2007 | |
| JP | 2007-521031 A | 8/2007 | |
| JP | 2007-537804 A | 12/2007 | |
| JP | 2008-125813 A | 6/2008 | |
| KR | 100458978 B1 | 5/2005 | |
| WO | WO-86/05966 A1 | 10/1986 | |
| WO | WO-88/00812 A1 | 2/1988 | |
| WO | WO-88/07666 A1 | 10/1988 | |

(56) References Cited

FOREIGN PATENT DOCUMENTS

| | | |
|---|---|---|
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |
| WO | WO-97/04707 A1 | 2/1997 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-97/42885 A1 | 11/1997 |
| WO | WO-97/42888 A1 | 11/1997 |
| WO | WO-97/43962 A1 | 11/1997 |
| WO | WO-98/00193 A1 | 1/1998 |
| WO | WO-98/31275 A1 | 7/1998 |
| WO | WO-98/35225 A1 | 8/1998 |
| WO | WO-99/12008 A1 | 3/1999 |
| WO | WO-99/23492 A1 | 5/1999 |
| WO | WO-99/44508 A1 | 9/1999 |
| WO | WO-99/56954 A1 | 11/1999 |
| WO | WO-99/58051 A1 | 11/1999 |
| WO | WO-99/62576 A1 | 12/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/19185 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/13795 A1 | 3/2001 |
| WO | WO-01/16575 A1 | 3/2001 |
| WO | WO-01/52727 A1 | 7/2001 |
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/078533 A2 | 10/2002 |
| WO | WO-02/078533 A3 | 10/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/007819 A1 | 1/2003 |
| WO | WO-2003/030984 A1 | 4/2003 |
| WO | WO-2003/066128 A2 | 8/2003 |
| WO | WO-2003/066128 A3 | 8/2003 |
| WO | WO-2003/070099 A1 | 8/2003 |
| WO | WO-2003/071940 A1 | 9/2003 |
| WO | WO-2003/071940 C1 | 9/2003 |
| WO | WO-03/088834 A1 | 10/2003 |
| WO | WO-2004/045375 A2 | 6/2004 |
| WO | WO-2004/045375 A3 | 6/2004 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2004/085995 A2 | 10/2004 |
| WO | WO-2004/085995 A3 | 10/2004 |
| WO | WO-2004/091693 A2 | 10/2004 |
| WO | WO-2004/091693 A3 | 10/2004 |
| WO | WO-2004/105827 A2 | 12/2004 |
| WO | WO-2004/105827 A3 | 12/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/013824 A1 | 2/2005 |
| WO | WO-2005/016125 A2 | 2/2005 |
| WO | WO-2005/018709 A2 | 3/2005 |
| WO | WO-2005/018709 A3 | 3/2005 |
| WO | WO-2005/018710 A2 | 3/2005 |
| WO | WO-2005/018710 A3 | 3/2005 |
| WO | WO-2005/054840 A1 | 6/2005 |
| WO | WO-2005/084543 A1 | 9/2005 |
| WO | WO-2005/084546 A2 | 9/2005 |
| WO | WO-2005/084546 A3 | 9/2005 |
| WO | WO-2005/085995 A1 | 9/2005 |
| WO | WO-2005/112763 A1 | 12/2005 |
| WO | WO-2006/031920 A2 | 3/2006 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |
| WO | WO-2007/054317 A1 | 5/2007 |
| WO | WO-2007/108519 A1 | 9/2007 |
| WO | WO-2007/112034 A2 | 10/2007 |
| WO | WO-2007/112034 A3 | 10/2007 |
| WO | WO-2008/027319 A2 | 3/2008 |
| WO | WO-2008/027319 A3 | 3/2008 |
| WO | WO-2008/062648 A1 | 5/2008 |
| WO | WO-2009/145920 A1 | 12/2009 |
| WO | WO-2009/148624 A1 | 12/2009 |
| WO | WO-2009/148626 A1 | 12/2009 |
| WO | WO-2011/065981 A1 | 6/2011 |
| WO | WO-2011/162823 A1 | 12/2011 |
| WO | WO-2013/020103 A1 | 2/2013 |
| WO | WO-2014/205412 A1 | 12/2014 |
| WO | WO-2018/191700 A1 | 10/2018 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Brazzle, J. et al. Active Microneedles with Integrated Functionality, Solid-State Sensor and Actuator Workshop, Hilton Head Island, South Carolina, Jun. 4-8, 2000, Technical Digest, 199-202.

Burge, M.R., (Aug. 2001). "Lack of Compliance with Home Blood Glucose Monitoring Predicts Hospitalization in Diabetes", Diabetes Care 24(8): 1502-1503.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1981). "Evaluation of a New Reflectance Photometer for Use in Home Blood Glucose Monitoring," *Diabetes Care*, 4(5):547-550.

(56) References Cited

OTHER PUBLICATIONS

Clarke, W.L. et al. (Sep.-Oct. 1987). "Evaluating Clinical Accuracy of Systems for Self-Monitoring of Blood Glucose," *Diabetes Care* 10(5):622-628.
Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.
Coster, S. et al. (2000). "Monitoring Blood Glucose Control in Diabetes Mellitus: A Systematic Review." *Health Technology Assessment* 4(12):1-93.
Cox, D.J. et al. (Jun. 1997). "Understanding Error Grid Analysis," *Diabetes Care* 20(6):911-912.
D'Arrigo, T.D. (Mar. 2000). "GlucoWatch Monitor Poised for Approval," *Diabetes Forecast*, 53(3):43-44.
Extended European Search Report dated Feb. 2, 2016 for European Patent Application No. 15187274.4, filed on Sep. 29, 2015, 6 pages.
Extended European Search Report dated Apr. 19, 2011, for EP Application No. 10 18 0848.3 filed Sep. 28, 2010, 5 pages.
Extended European Search Report dated Feb. 22, 2012, for EP Application No. EP 10 18 1155, filed Sep. 28, 2010, six pages.
Extended European Search Report dated Jan. 22, 2013, for EP Application No. 12182900.6, filed on Sep. 29, 2006, 6 pages.
Extended European Search Report dated Apr. 29, 2013 for EP Patent Application No. 12192620.8, filed on Nov. 14, 2012, 8 pages.
Extended European Search Report dated Nov. 8, 2016, for EP Application No. 16 167 087.2, filed on Aug. 3, 2012, 6 pages.
Extended European Search Report dated Jun. 8, 2011, for EP Application No. 07 837 337.0, filed on Aug. 27, 2007, 5 pages.
Feldman, B. et al. (2000). "FreeStyle™: A Small-Volume Electrochemical Glucose Sensor for Home Blood Glucose Testing," *Diabetes Technology and Therapeutics*, 2(2):221-229.
Final Office Action dated Mar. 30, 2015, for U.S. Appl. No. 12/457,085, filed Jun. 1, 2009, 14 pages.
Final Office Action dated Aug. 3, 2016, for U.S. Appl. No. 12/457,085, filed Jun. 1, 2009, 13 pages.
Final Office Action dated Jul. 9, 2008, for U.S. Appl. No. 11/529,613, filed Sep. 29, 2006, 19 pages.
Final Office Action dated Nov. 23, 2009, for U.S. Appl. No. 11/529,613, filed Sep. 29, 2006, 20 pages.
Final Office Action dated Jan. 21, 2011, for U.S. Appl. No. 11/529,613, filed Sep. 29, 2006, 7 pages.
Final Office Action dated Apr. 13, 2016, for U.S. Appl. No. 13/669,366, filed Nov. 5, 2012, 31 pages.
Final Office Action dated Aug. 15, 2013, for U.S. Appl. No. 13/562,129, filed Jul. 30, 2012, 12 pages.
Final Office Action dated Aug. 28, 2014, for U.S. Appl. No. 13/562,129, filed Jul. 30, 2012, 11 pages.
Final Office Action dated Dec. 26, 2014, for U.S. Appl. No. 13/669,366, filed Nov. 5, 2012, 9 pages.
Final Office Action dated Jan. 22, 2014, for U.S. Appl. No. 13/669,366, filed Nov. 5, 2012, 8 pages.
Final Office Action dated Jun. 30, 2010, for U.S. Appl. No. 11/529,612, filed Sep. 29, 2006, 11 pages.
Final Office Action dated May 30, 2007, for U.S. Appl. No. 11/125,107, filed May 10, 2005, 11 pages.
Final Office Action dated Nov. 1, 2010, for U.S. Appl. No. 11/311,667, filed Dec. 20, 2005, 9 pages.
Final Office Action dated Nov. 21, 2011, for U.S. Appl. No. 11/311,667, filed Dec. 20, 2005, 8 pages.
Final Office Action dated Jun. 11, 2010, for U.S. Appl. No. 11/529,614, filed Sep. 29, 2006, 16 pages.
Final Office Action dated Mar. 10, 2015, for U.S. Appl. No. 11/529,614, filed Sep. 29, 2006, 24 pages.
Final Office Action dated Dec. 16, 2008, for U.S Appl. No. 11/510,784, filed Aug. 28, 2006, 15 pages.
Final Office Action dated Jul. 26, 2010, for U.S. Appl. No. 11/510,784, filed Aug. 28, 2006, 30 pages.
Hemmerich, K.J. et al. (Apr. 1995)."Guide to Engineering Thermoplastics," Medical Devices and Diagnostic Industry pp. 39-59.
Integ. (2000). "LifeGuide™ Glucose Meter. No Lancets. No Blood," located at <http://www.integonline.com>, last visited May 1, 2000, 10 pages.
International Search Report dated Jul. 16, 2009, for PCT Application No. PCT/US2009/003318 filed on Jun. 1, 2009, 3 pages.
International Search Report dated May 2, 2007, for PCT Application No. PCT/US2006/37923, filed on Sep. 9, 2006, 1 page.
International Search Report dated Dec. 3, 2004, for PCT Application No. PCT/US2004/08798, filed on Mar. 24, 2004, 3 pages.
International Search Report dated Aug. 16, 2007 for PCT Application No. PCT/US2006/038163, filed on Sep. 29, 2006, 1 page.
International Search Report dated Aug. 7, 2007 for PCT/US2006/38049, filed on Sep. 29, 2006, 1 page.
International Search Report dated Oct. 19, 2012 for PCT Application No. PCT/US2012/049629, filed on Aug. 3, 2012, 3 pages.
International Search Report dated Mar. 3, 2008, for PCT Application No. PCT/US2007/018780, filed on Aug. 27, 2007, 2 pages.
Ishii H. et al., (Aug. 2001). "Seasonal Variation of Glycemic Control in Type 2 Diabetic Patients", Diabetes Care 24(8):1503.
Johnson, R.N. et al. (Jan. 1998). "Accuracy of Devices Used for Self-Monitoring of Blood Glucose," *Annals of Clinical Biochemistry* 35(1):68-74.
Johnson, R.N. et al. (Jan. 1999). "Analytical Error of Home Glucose Monitors: A Comparison of 18 Systems," *Annals of Clinical Biochemistry* 36(1):72-79.
Johnson, R.N. et al. (2001). "Error Detection and Measurement In Glucose Monitors," *Clinica Chimica Acta* 307:61-67.
Kumetrix, Inc. (Dec. 1999). "Painless Blood Glucose Monitoring, Courtesy of the Mosquito," *Start-Up* pp. 27-28.
Lee, S-C. (Jun. 1999). "Light Scattering by Closely Spaced Parallel Cylinders Embedded in a Finite Dielectric Slab," *Journal of the Optical Society of America A* 16(6):1350-1361.
Massey V et al. (Aug. 1960). "Studies on the Reaction Mechanism of Lipoyl Dehydrogenase" Biochim. Biophys. Acta 48: 33-47.
McGarraugh, G. et al. (2001). "Physiological Influences on Off-Finger Glucose Testing," *Diabetes Technology & Therapeutics* 3(3):367-376.
McNichols, R.J. et al. (Jan. 2000). "Optical Glucose Sensing in Biological Fluids: An Overview," *Journal of Biomedical Optics*, 5(1):5-16.
Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.
Medline Plus. (Jun. 17, 2008). Medical Encyclopedia, Monitor Blood Glucose-Series: Part 1-4, 6 pages.
Neeley, W.E. et al. (1981). "An Instrument for Digital Matrix Photometry," *Clinical Chemistry* 27(10):1665-1668.
Neeley, W.E. (1983). "Reflectance Digital Matrix Photometry," *Clinical Chemistry* 29(6):1038-1041.
Neeley, W.E. (1983). "Multilayer Film Analysis for Glucose in 1-μL Samples of Plasma," *Clinical Chemistry* 29(12):2103-2105.
Neeley, W.E. (1988). "A Reflectance Photometer with a Square Photodiode Array Detector for Use on Multilayer Dry-Film Slides," *Clinical Chemistry* 34(11):2367-2370.
Non-Final Office Action dated Oct. 8, 2015, for U.S. Appl. No. 12/457,085, filed Jun. 1, 2009, 11 pages.
Non-Final Office Action dated Dec. 12, 2007, for U.S. Appl. No. 11/529,613, filed Sep. 29, 2006, 13 pages.
Non-Final Office Action dated Apr. 28, 2009, for U.S. Appl. No. 11/529,613, filed Sep. 29, 2006, 21 pages.
Non-Final Office Action dated Jun. 4, 2010, for U.S. Appl. No. 11/529,613, filed Sep. 29, 2006, 23 pages.
Non-Final Office Action dated Mar. 23, 2012, for U.S. Appl. No. 13/197,592, filed Aug. 3, 2011, 7 pages.
Non-Final Office Action dated Mar. 23, 2012, for U.S. Appl. No. 13/197,603, filed Aug. 3, 2011, 6 pages.
Non-Final Office Action dated Nov. 26, 2012 for U.S. Appl. No. 13/562,129, filed Jul. 30, 2012, 9 pages.
Non Final Office Action dated Apr. 8, 2015, for U.S. Appl. No. 13/566,886, filed Aug. 3, 2012, 11 pages.
Non Final Office Action dated Apr. 12, 2011, for U.S. Appl. No. 11/311,667, filed Dec. 20, 2005, 7 pages.

(56) References Cited

OTHER PUBLICATIONS

Non Final Office Action dated Aug. 5, 2014, for U.S. Appl. No. 13/669,366, filed Nov. 5, 2012, 8 pages.
Non Final Office Action dated Dec. 5, 2014, for U.S. Appl. No. 13/562,129, filed Jul. 30, 2012, 7 pages.
Non Final Office Action dated Jan. 12, 2009, for U.S. Appl. No. 11/529,612, filed Sep. 29, 2006, 9 pages.
Non Final Office Action dated Jan. 21, 2011, for U.S. Appl. No. 11/529,612, filed Sep. 29, 2006, 9 pages.
Non Final Office Action dated Jul. 13, 2010, for U.S. Appl. No. 12/222,724, filed Aug. 14, 2008, 11 pages.
Non Final Office Action dated Jul. 31, 2015, for U.S. Appl. No. 13/669,366, filed Nov. 5, 2012, 16 pages.
Non Final Office Action dated Mar. 21, 2014, for U.S. Appl. No. 13/562,129, filed Jul. 30, 2012, 12 pages.
Non Final Office Action dated Mar. 25, 2011, for U.S. Appl. No. 12/222,724, filed Aug. 14, 2008, 13 pages.
Non Final Office Action dated Mar. 5, 2010, for U.S. Appl. No. 11/311,667, filed Dec. 20, 2005, 8 pages.
Non Final Office Action dated May 14, 2008, for U.S. Appl. No. 11/529,612, filed Sep. 29, 2006, 9 pages.
Non Final Office Action dated May 16, 2013, for U.S. Appl. No. 13/669,366, filed Nov. 5, 2012, 8 pages.
Non Final Office Action dated May 5, 2005, for U.S. Appl. No. 10/131,268, filed Apr. 23, 2002, 8 pages.
Non Final Office Action dated Nov. 2, 2006, for U.S. Appl. No. 11/125,107, filed May 10, 2005, 10 pages.
Non Final Office Action dated Oct. 14, 2009, for U.S. Appl. No. 11/529,612, filed Sep. 29, 2006, 10 pages.
Non Final Office Action dated Oct. 3, 2008, for U.S. Appl. No. 10/722,074, filed Nov. 24, 2003, 10 pages.
Non-Final Office Action dated Dec. 17, 2015, for U.S. Appl. No. 11/529,614, filed Sep. 29, 2006, 6 pages.
Non Final Office Action dated Dec. 2, 2004, for U.S. Appl. No. 10/347,620, filed Jan. 22, 2003, 8 pages.
Non-Final Office Action dated Jan. 27, 2009, for U.S. Appl. No. 11/529,614, filed Sep. 29, 2006, 17 pages.
Non-Final Office Action dated Jan. 6, 2014, for U.S. Appl. No. 11/529,614, filed Sep. 29, 2006, 12 pages.
Non-Final Office Action dated Jun. 21, 2013, for U.S. Appl. No. 13/752,261, filed Jan. 28, 2013, 12 pages.
Non-Final Office Action dated Jun. 6, 2008, for U.S. Appl. No. 11/529,614, filed Sep. 29, 2006, 17 pages.
Non-Final Office Action dated Oct. 9, 2014, for U.S. Appl. No. 14/446,262, filed Jul. 29, 2014, 15 pages.
Non Final Office Action dated Sep. 29, 2004, for U.S. Appl. No. 10/394,230, filed Mar. 24, 2003, 10 pages.
Non-Final Office Action dated Dec. 19, 2007, for U.S. Appl. No. 11/510,784, filed Aug. 28, 2006, 17 pages.
Non-Final Office Action dated May 11, 2009, for U.S Appl. No. 11/510,784, filed Aug. 28, 2006, 13 pages.
Non-Final Office Action dated Jan. 13, 2010, for U.S. Appl. No. 11/510,784, filed Aug. 28, 2006, 18 pages.
Non-Final Office Action dated Aug. 11, 2011, for U.S. Appl. No. 11/510,784, filed Aug. 28, 2006, 35 pages.
Notice of Allowance dated Oct. 3, 2012, for U.S. Appl. No. 11/510,784, filed Aug. 28, 2006, 10 pages.
Notice of Allowance dated Apr. 18, 2012, for U.S. Appl. No. 11/529,612, filed Sep. 29, 2006, 8 pages.
Notice of Allowance dated Apr. 19, 2010, for U.S. Appl. No. 29/338,117, filed Jun. 4, 2009, 4 pages.
Notice of Allowance dated Aug. 3, 2012, for U.S. Appl. No. 11/529,612, filed Sep. 29, 2006, 5 pages.
Notice of Allowance dated Jan. 14, 2010, for U.S. Appl. No. 29/338,117, filed Jun. 4, 2009, 4 pages.
Notice of Allowance dated Jun. 29, 2012, for U.S. Appl. No. 11/311,667, filed Dec. 20, 2005, 5 pages.
Notice of Allowance dated Mar. 14, 2012, for U.S. Appl. No. 12/222,724, filed Aug. 14, 2008, 7 pages.

Notice of Allowance dated Mar. 27, 2015, for U.S. Appl. No. 13/562,129, filed Jul. 30, 2012, 7 pages.
Notice of Allowance dated Mar. 31, 2005, for U.S. Appl. No. 10/394,230, filed Mar. 24, 2003, 10 pages.
Notice of Allowance dated May 15, 2008, for U.S. Appl. No. 11/125,107, filed May 10, 2005, 7 pages.
Notice of Allowance dated May 28, 2009, for U.S. Appl. No. 29/300,933, filed May 30, 2008, 6 pages.
Notice of Allowance dated Nov. 23, 2011, for U.S. Appl. No. 12/222,724, filed Aug. 14, 2008, 7 pages.
Notice of Allowance dated Nov. 27, 2012, for U.S. Appl. No. 11/529,612, filed Sep. 29, 2006, 5 pages.
Notice of Allowance dated Nov. 29, 2005, for U.S. Appl. No. 10/131,268, filed Apr. 23, 2002, 6 pages.
Notice of Allowance dated Oct. 12, 2011, for U.S. Appl. No. 11/529,612, filed Sep. 29, 2006, 8 pages.
Notice of Allowance dated Feb. 23, 2015, for U.S. Appl. No. 14/446,262, filed Jul. 29, 2014, 8 pages.
Notice of Allowance dated Feb. 5, 2014, for U.S. Appl. No. 13/752,261, filed Jan. 28, 2013, 9 pages.
Notice of Allowance dated Jun. 15, 2009, for U.S. Appl. No. 10/722,074, filed Nov. 24, 2003, 6 pages.
Notice of Allowance dated Mar. 2, 2016, for U.S. Appl. No. 11/529,614, filed Sep. 29, 2006, 12 pages.
Notice of Allowance dated Mar. 28, 2005, for U.S. Appl. No. 10/347,620, filed Jan. 22, 2003, 6 pages.
Notice of Allowance dated May 3, 2011, for U.S. Appl. No. 11/529,613, filed Sep. 29, 2006, 12 pages.
Otto, E. et al. (2000). "An Intelligent Diabetes Software Prototype: Predicting Blood Glucose Levels and Recommending Regimen Changes," *Diabetes Technology and Therapeutics* 2(4):569-576.
Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.
Princen, H.M. (May 1969). "Capillary Phenomena in Assemblies of Parallel Cylinders, I. Capillary Rise Between Two Cylinders," *Journal of Colloid and Interface Science* 30(1):69-75.
Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Rosen, S. (1999). "Road to New-Age Glucose Monitoring Still Rocky," *Diagnostic Insight*, pp. 4-5, 12-13, 16.
Smart, W.H. et al. (2000). "The Use of Silicon Microfabrication Technology in Painless Glucose Monitoring,"*Diabetes Technology & Therapeutics* 2(4):549-559.
Spielman, A. et al. (2001). *Mosquito: A Natural History of Our Most Persistent and Deadly Foe*, First Edition, Hyperion, New York, NY, 3 pages. (Table of Contents Only).
Sonntag, O. (1993). Ektachem. Dry Chemistry, Analysis With Carrier-Bound Reagents, Elsevier Science Publishers, 57 pages.
Straub F.B. (Mar. 1939). "Isolation and Properties of a flavoprotien from Heart Muscle Tissue", Biochemical Journal 33: 787-792.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Tietz, N.W. (1986). Textbook of Clinical Chemistry, W.B. Saunders Company, pp. 1533 and 1556.
Trinder, P. (1969). "Determination of Glucose in Blood Using Glucose Oxidase with an Alternate Oxygen Acceptor," *Annals of Clinical Biochemistry* 6:24-28.
U.S. Precision Lens, Inc. (1983).The Handbook of Plastic Optics.
Written Opinion dated Jul. 16, 2009, for PCT Application No. PCT/US2009/003318 filed on Jun. 1, 2009, 8 pages.
Written Opinion dated May 2, 2007, for PCT Application No. PCT/US2006/37923, filed on Sep. 9, 2006, 5 pages.

(56) References Cited

OTHER PUBLICATIONS

Written Opinion dated Dec. 3, 2004, for PCT Application No. PCT/US2004/08798, filed on Mar. 24, 2004, 4 pages.
Written Opinion dated Aug. 17, 2007 for PCT/US2006/38049, filed on Sep. 29, 2006, 6 pages.
Written Opinion dated Aug. 16, 2007 for PCT Application No. PCT/US2006/038163, filed on Sep. 29, 2006, 4 pages.
Written Opinion dated Oct. 19, 2012 for PCT Application No. PCT/US2012/049629, filed on Aug. 3, 2012, 7 pages.
Written Opinion of the International Searching Authority dated Mar. 3, 2008, for PCT Application No. PCT/US2007/018780, filed on Aug. 27, 2007, 7 pages.
Yum, S. I. et al. (Nov. 1, 1999). "Capillary Blood Sampling for Self-Monitoring of Blood Glucose," *Diabetes Technology & Therapeutics*, 1(1):29-37.
Notice of Allowance dated Aug. 2, 2017, for U.S. Appl. No. 12/457,085, filed Jun. 1, 2009, 23 pages.
Extended European Search Report dated Nov. 8, 2016, from the European Patent Office for EP Application No. 16167087.2, filed on Aug. 3, 2012, 6 pages.
Non-Final Office Action dated Dec. 16, 2016, for U.S. Appl. No. 13/566,886, filed Aug. 3, 2012, 11 pages.
Non-Final Office Action dated Mar. 20, 2017, by The United States Patent and Trademark Office for U.S. Appl. No. 15/191,434, filed Jun. 23, 2016, 20 pages.
Non-Final Office Action dated Jun. 20, 2017, for U.S. Appl. No. 15/191,434, filed Jun. 23, 2016, 20 pages.
Notice of Allowance dated Aug. 18, 2017, for U.S. Appl. No. 13/566,886, filed Aug. 3, 2012, 10 pages.
Corrected Notice of Allowance dated Nov. 1, 2017, for U.S. Appl. No. 12/457,085, filed Jun. 1, 2009, 2 pages.
Khalil, "Non-invasive glucose measurement technologies: an update from 1999 to the dawn of the new millennium," Diabetes Technology & Therapeutics., vol. 6, No. 5, 2004.
Non-Final Office Action dated Aug. 7, 2020, for U.S. Appl. No. 15/697,311, filed Sep. 6, 2017, 10 pages.
Extended European Search Report dated Nov. 10, 2020, for European Application No. 20169957.6, filed on Aug. 3, 2012, 9 pages.

\* cited by examiner

FIG. 22
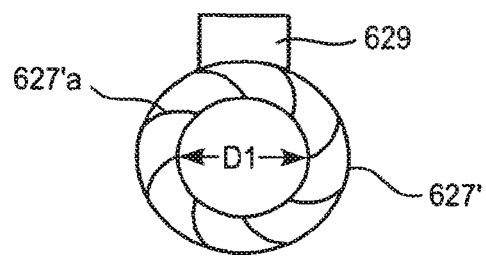
FIG. 23
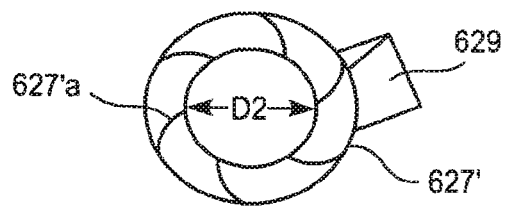
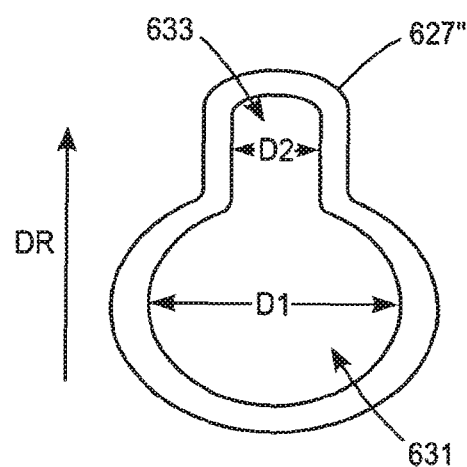
FIG. 24

BODY FLUID SAMPLING DEVICE-SAMPLING SITE INTERFACE

CROSS-REFERENCE TO RELATED APPLICATIONS

This application is a continuation of U.S. patent application Ser. No. 12/457,085, filed on Jun. 1, 2009, now issued as U.S. Pat. No. 9,833,183 on Dec. 5, 2017, which claims priority to U.S. Provisional Patent Application No. 61/129,025, filed on May 30, 2008.

FIELD

The present invention relates to devices, arrangements and methods involving body fluid acquisition. In certain embodiments, the present invention is directed to an interface member for contacting the skin of the user of a body fluid sampling device.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

According to the American Diabetes Association, diabetes is the fifth-deadliest disease in the United States. Since 1987 the death rate due to diabetes has increased by 45 percent. There are an estimated 20.8 million children and adults in the United States, or 7% of the population, who have diabetes. The total annual economic cost of diabetes in 2007 was estimated to be $174 billion. This is an increase of $42 billion since 2002. This 32% increase means the dollar amount has risen over $8 billion each year.

A critical component in managing diabetes is frequent blood glucose monitoring. Currently, a number of systems exist for self-monitoring by the patient. Most fluid analysis systems, such as systems for analyzing a sample of blood for glucose content, comprise multiple separate components such as separate lancing, transport, and quantification portions. These systems are bulky, and often confusing and complicated for the user. The systems require significant user intervention.

Technology in the field of self-monitoring of blood glucose has placed the burden of acquiring sufficient blood for conducting a test on the user of the technology. Earlier versions of consumer-oriented self-monitoring products usually required many microliters of blood.

Lancing devices and the lancets themselves have also evolved somewhat over the past few decades. Some lancing mechanisms may produce relatively less pain by either (1) projecting the lancet in and out of the skin in a more straight path and thus reducing stimulation of percutaneous nerves which provide the pain stimulus; and (2) offering depth control in the lancing device so that the user may balance the expression of sufficient blood against the level of pain. Furthermore, lancet manufacturers offer a variety of lancet sizes, lengths, and tip bevel patterns with some companies claiming that their lancet is less painful than others.

What remains clear is that the most testers, when lancing at the finger, often must put down the lancing device after creating a wound and apply pressure near the finger tip in order to produce sufficient blood for the test strip in the meter. Many instructions for use of conventional meter systems specifically prescribe that the user perform this "milking" process because without it, many will not spontaneously produce the required volume. Applicants have observed this phenomenon in the use of commonly available commercial sampling and meter systems. In one study, when a trained professional lanced the finger tips of 16 volunteer diabetic subjects at the maximum depth setting on commercially available device under controlled conditions, only 15% of lanced sites spontaneously produced sufficient blood for the meter to accurately measure glucose levels.

Conventional sampling devices and methods are overly reliant upon user intervention, such as milking, in order to consistently express a sufficient quantity of blood from the wound site. Thus, it would be advantageous to provide constructions, arrangements and techniques that improved the ability to consistently and spontaneously obtain an adequate sample of body fluid from a sampling site on the skin of the user.

SUMMARY OF THE INVENTION

According to the present invention, there are provided constructions, arrangements and techniques that may address one or more of the above-mentioned objectives. However, the present invention is not limited to the context of blood sampling performed for the purposes of monitoring glucose concentration. Numerous alternative applications or uses for the concepts described herein are contemplated.

According to certain aspects of the present invention, there are provided constructions, arrangements and techniques that may optionally provide one or more of the following benefits or advantages: increase in the likelihood of a spontaneous production of blood from a wound created by a skin-penetrating member; providing the user with a tactile and visual aid for correctly positioning the device or arrangement; creating a sufficient seal between the skin at the sampling site and one or more components of the arrangement; and reduction or mitigation of pain sensation.

As used herein "digital" means fingers or toes. "Digital body fluid" means expression of body fluid from a wound created on the fingers or toes, and encompasses lancing sites on the dorsal or palm side of the distal finger tips.

As used herein, "body fluid" encompasses whole blood, intestinal fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid.

It is to be understood that reference herein to first, second, third and fourth components (etc.) does not limit the present invention to embodiments where each of these components is physically separable from one another. For example, a single physical element of the invention may perform the functions of more than one of the claimed first, second, third or fourth components. Conversely, a plurality of separate physical elements working together may perform the functions of one of the claimed first, second, third or fourth components. Similarly, reference to first, second (etc.) method steps does not limit the invention to only separate steps. According to the invention, a single method step may satisfy multiple steps described herein. Conversely, a plurality of method steps could, in combination, constitute a single method step recited herein. In addition, the steps of the method are not necessarily limited to the order in which they are described or claimed herein.

According to one aspect, the present invention is directed to an arrangement for producing a sample of body fluid from a wound opening created in a skin surface at a sampling site, the arrangement comprising: a housing, the housing comprising a first opening; a skin interface member disposed in the first opening, the skin interface member comprising an inner member having a second opening, and an outer member at least partially surrounding the inner member and attached to the first opening; and at least one skin-penetration member configured and arranged to project within the second opening.

According to another aspect, the present invention is directed to an arrangement for producing a sample of body fluid from a wound opening created in a skin surface at a sampling site, the arrangement comprising: a housing, the housing comprising a first opening; a skin interface member disposed in the first opening, the skin interface member comprising an inner portion having a second opening, the inner portion further comprising a first projection along the second opening and a second projection along the second opening, the first and second projections extending in opposite directions, and the skin interface member further comprising an outer portion at least partially surrounding the inner portion and attached to the first opening; at least one skin-penetration member configured and arranged to project within the second opening; a cartridge disposed within the housing, wherein the at least one skin-penetration member is disposed within the cartridge.

According to a further aspect, the present invention provides an arrangement for producing a sample of body fluid from a wound opening created in a skin surface at a sampling site, the arrangement comprising: a housing, the housing comprising a first opening; a skin interface member disposed in the second opening, the skin interface member comprising a longitudinally tapered cylindrical member having a first opening constructed an arranged to be contacted by the skin, the inner diameter of the cylinder decreasing along the longitudinal direction away from the second opening, the longitudinally tapered cylindrical member comprising a plurality of longitudinal slits thereby forming a plurality of longitudinal sections, the longitudinally tapered cylindrical member constructed and arranged so as to be movable within the first opening upon pressing against the surface of the skin at the second opening thereby forcing the longitudinal sections radially inward; and at least one skin-penetration member configured and arranged to project within the second opening.

According to yet another aspect, the present invention provides an arrangement for producing a sample of body fluid from a wound opening created in a skin surface at a sampling site, the arrangement comprising: a housing, the housing comprising a first opening; a skin interface member disposed in the first opening, the skin interface member comprising a plurality of concentric telescoping sections, including an innermost section, the innermost section having a second opening, the innermost member constructed and arranged so as to be pressed against the surface of the skin at the second opening; and at least one skin-penetration member configured and arranged to project within the second opening.

According to an additional aspect, the present invention provides an arrangement for producing a sample of body fluid from a wound opening created in a skin surface at a sampling site, the arrangement comprising: a housing, the housing comprising a first opening; a skin interface member disposed in the first opening, the skin interface member comprising a plurality of rotatable members defining a gap therebetween, the plurality of rotatable members constructed an arranged such that rotatable members are forced toward one another upon being pressed against the skin thereby decreasing the gap and pinching the skin; and at least one skin-penetration member configured and arranged to project within the gap.

BRIEF DESCRIPTION OF THE DRAWING FIGURES

The following description of preferred embodiments can be read in connection with the accompanying drawings in which like numerals designate like elements and in which:

FIG. 22 is a partial perspective view of an arrangement formed according to a further embodiment of the present invention, in a first state.

FIG. 23 is a partial perspective of the arrangement of FIG. 22, in a second state.

FIG. 24 is a partial perspective view of an arrangement formed according to an additional alternative aspect of the present invention.

DETAILED DESCRIPTION

Figure 1:
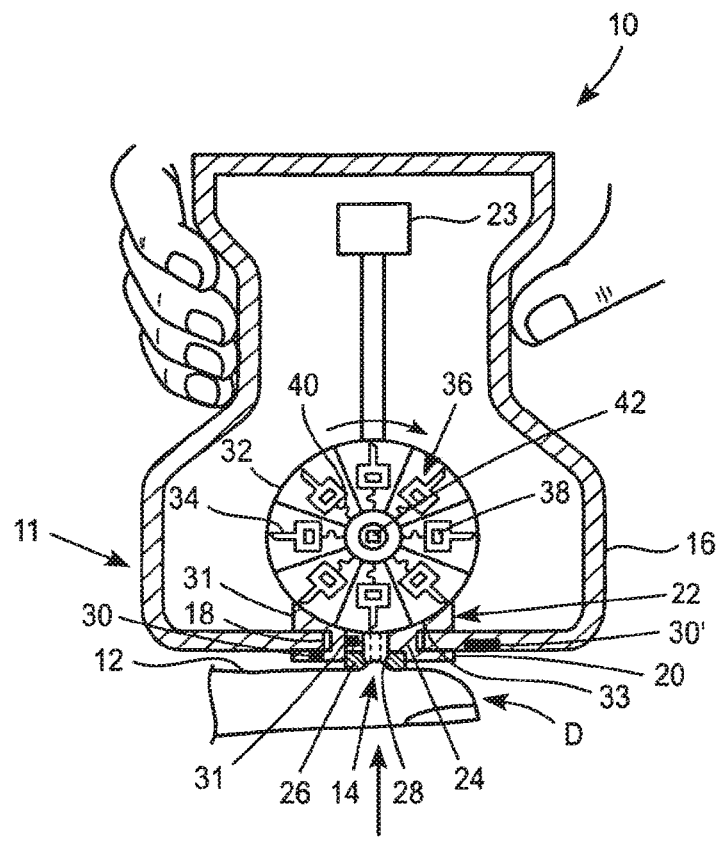
FIG. 1 is a cut away side view of an arrangement constructed according to the present invention.

According to a first aspect of the present invention, there are provided arrangements and techniques for reliably expressing body fluid from a digit or from an alternate site such as the forearm, thigh, etc. For example, according to the present invention, arrangements and techniques are provided which consistently and reliably express an amount of body fluid that is sufficient to perform an analysis to quantify the amount of an analyte (e.g., glucose, bilirubin, alcohol, controlled substances, toxins, hormones, proteins, etc.) contained therein.

One embodiment of an arrangement 10 of the type described above is illustrated in FIGS. 1-2. As illustrated therein, the arrangement 10 may be in the form of an integrated meter 11. It should be understood that any of the arrangements or embodiments described herein may be used in connection with an integrated meter, which may have one or more of the features of the integrated meter 11 of the embodiment illustrated in FIG. 1. However, it should be made clear that the present invention is not so limited. The concepts and arrangements described herein are believed to be applicable to a number of different devices and systems, such as simple lancing devices, multiple component systems, and the like.

The arrangements described herein may be used or applied to a skin surface 12 at a suitable sampling site 14. One suitable sampling site 14 is on a digit D. However, the arrangements described herein may be used or applied to any skin surface at any suitable sampling site which may include alternative sampling sites such as the forearm, thigh, etc.

According to the illustrated embodiment, the arrangement 10 includes a housing 16. The housing 16 may have any suitable shape or configuration, and is not limited to the shape and configuration illustrated. According to one alternative construction, the housing 16 may comprise at least a portion of a removable cap (not shown). The shape of the housing 16 may be contoured such that it is easily grasped by the hand of the user. The housing 16 can be constructed of any suitable material. For example, the housing 16 may be constructed of a polymeric or metallic material. The housing may comprise a first opening 18 disposed therein. A skin interface member 20 constructed according to the principles of the present invention may be disposed in the first opening 18 and provided with an attachment 22 to the housing 16. According to one embodiment, the attachment 22 is readily removable from the opening 18 in the housing 16, thereby allowing the user to remove an existing skin interface member 20 and insert a replacement or alternatively constructed skin interface members 20.

Figure 2:
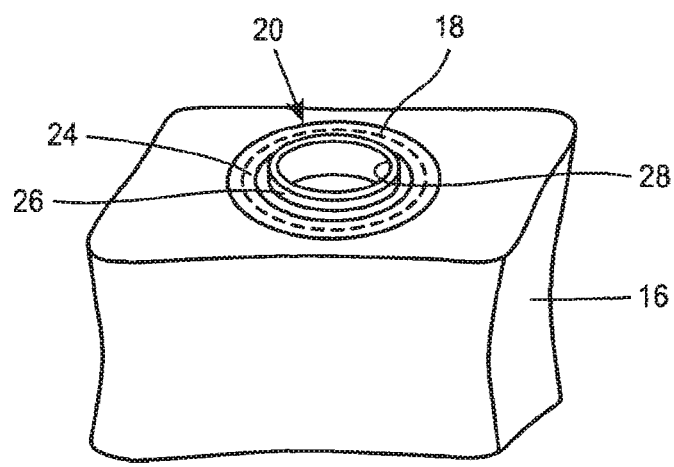
FIG. 2 is a partial bottom perspective view of the arrangement of FIG. 1.
Figure 3:
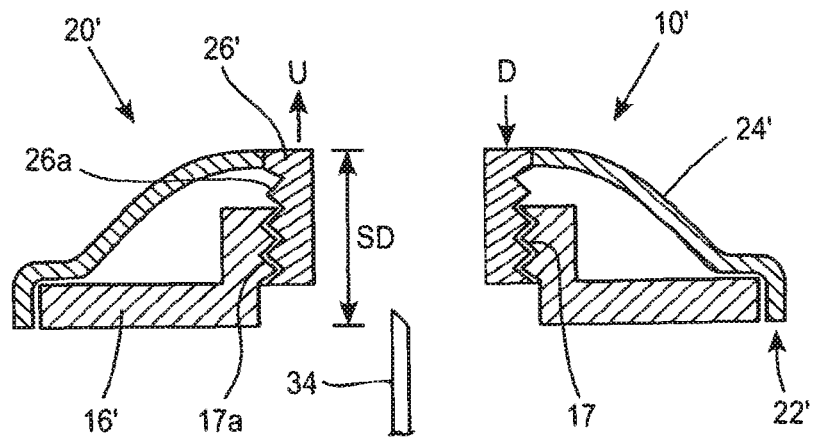
FIG. 3 is a partial sectional view of an alternative arrangement formed according to the present invention.

As illustrated in FIG. 1, the thickness of the skin interface member 20 defines a separation distance (e.g., SD, FIG. 3) between the housing 16 and the surface of the skin 12. Thus, this separation distance can be changed by changing the thickness of the skin interface member, which in turn will alter the depth of penetration of a skin penetration member traveling from within the housing and into the surface of the skin, as will be described in greater detail below. Therefore, according to the principles of the present invention, a number of different skin interface members 20 having different thicknesses can be provided to the user so that an appropriate penetration depth of a skin penetration member can be selected by substituting a skin interface member 20 having an appropriate thickness.

The arrangements described herein may further optionally include a catalyst to assist in the sample acquisition process by enhancing or facilitating perfusion of body fluid at a sampling site. At least one of several catalysts may be utilized or included in the arrangement of the present invention. Possible catalysts include, heat, pressure, vacuum, vibration, and topical drugs (which induce vasodilatation and increases the blood or body fluid available at the lancing site). These catalysts may be applied before, during, after lancing, or in combination with some or all three, to facilitate expression of sufficient quantity of body fluid for determination of the concentration of an analyte contained therein (e.g., glucose).

Skin interface member contact pressure is another catalyst and can be varied by a number of possible techniques. One such technique is to vary the size of an opening of the skin interface member. Another form of pressure catalyst can take the form of a squeezing or pinching member(s), as illustrated by examples which will be described herein.

Heat is another optional catalyst. Applying heat, thereby increasing the skin temperature at the wound site, increases blood production. Possible implementations of heat include infrared (IR) lights, or resistive elements to heat the skin.

Another catalyst is vacuum pressure. According to certain embodiments, a light vacuum (e.g., 3-8 in. Hg) is applied to surface of the skin 12 at the sampling site 14 before, during, and/or after lancing. Several embodiments for applying vacuum to the wound site are contemplated. One embodiment uses a motor driven pump 23 (FIG. 1) to apply vacuum to the area of the skin 12 at the sampling site 14. Alternative embodiments include using individually packaged vacuum chambers to apply vacuum, or using a rigid syringe like mechanism to apply vacuum.

According to the principles of the present invention, one or more of the above-described catalysts can be used in combination with each other, either concurrently or sequentially.

A skin interface member 20 may take any suitable form. For example, according to the illustrated embodiment, the skin interface member 20 comprises an outer member 24, which may include the aforementioned attachment structure 22 that affixes the skin interface member 20 to the housing, and an inner member 26. The inner member 26 comprises a second opening 28. The second opening 28 can take any suitable size and/or geometry. For example, the second opening 28 can be substantially circular or ovular, and have a diameter of about 3 mm-8 mm. According to a further alternative embodiment, the second opening 28 has a diameter of about 6 mm. The outer member 24 at least partially surrounds the inner member 26 and is attached thereto. Any suitable form of attachment is contemplated. For example, the outer member 24 and inner member 26 may be connected via an adhesive, or maybe integrated together via a co-molding process or similar integration technique. According to one embodiment, the inner member 26 has a first hardness, and the outer member 24 has a second hardness, wherein the first hardness is greater than the second hardness. The inner and outer members 26, 24 can be formed from any suitable materials. For example, the outer member 24 can be formed from an elastomer, silicone rubber, or soft plastic. The inner member 26 may be formed from a metal, plastic, relatively hard elastomer or ceramic.

Applicants have discovered that by providing the skin interface member 20 with a relatively harder inner member 26, a number of advantages are obtained. For instance, it has been observed that a skin interface member having a relatively harder inner member forms a better more reliable seal with the surface of the skin compared to a skin interface member formed entirely from a relatively soft pliable material. It has also been observed that many users prefer the tactile feel of the relatively hard inner member 26 when applied to the surface of the skin. This improved tactile feel also facilitates the correct positioning of the skin interface member for body fluid sampling.

The arrangements described herein may have a number of additional optional features. For example, at least one of the outer or inner members 24, 26 may have a construction so as to emit visible light thereby facilitating use of the arrangements in low-light conditions. Alternatively, the housing 16 may be provided with such a mechanism for emitting visible light. Optionally, the area of the housing in proximity to skin interface member 20 may be provided with the aforementioned light-emitting mechanism. Any number of mechanisms that emit visible light can be provided. For example, a portion of the housing 16 or at least one of the outer or inner members 24, 26 may be formed from a fluorescent material. Alternatively, one or more light emitting elements, such as light emitting diodes, schematically illustrated as elements 30 and 30', can be mounted within at least one of the housing 16 or outer and inner members 24, 26.

One or more members for generating heat may be incorporated into the skin interface member 20 of the present invention. Thus, for example, resistive heating elements, also generically illustrated as element 30, may be embedded within at least one of the outer and inner members 24, 26.

At least one of the outer and inner members 24, 26 may be provided with a textured surface for improving the tactile feel when applied to the skin of the user.

At least one sensor, generically illustrated as element 31, may also be provided for detecting contact with the skin of the user, and/or the amount of pressure exerted between the skin and the interface member 20 and/or the arrangement 10. Thus, for example, based on information derived from the sensor 31, the arrangement 10 can provide audible and/or visible feedback to the user to indicate when a target or optimal pressure is being applied to the skin 12 at the sampling site 14, and/or when the pressure being applied by the user lies outside of the target pressure value or range. Moreover, the arrangement 10 can be configured to use information derived from the sensor 31 to initiate one or more functions or operations. For example, an automated test sequence can be initiated once a minimum amount of force is sensed between the skin and the interface member 20, or if contact with the skin is sensed for a predetermined period of time. According to a further alternative embodiment, if no contact with the skin is sensed, the arrangement may automatically initiate a stand-by or shut down mode. Optionally, if no contact with the skin is sensed, the arrangement may automatically cover or close the second opening 28, so as to shield the inside of the arrangement 10 from the external environment and/or ambient light. The sensor can be located in any suitable portion of the arrangement, such as in the outer or inner member 24, 26, and/or the housing 16. The at least one sensor 31 can comprise, for example, well-known pressure transducer technology, capacitive touch sensing technology, resistive touch sensing technology, simple dome switch, or other micro switch, and the arrangement may further comprise additional signal processing and control components that are conventional in the art.

According to a further optional aspect, at least the inner member 26 of the skin interface member 20 can be provided with a hydrophobic property. This can be accomplished by forming the inner member entirely of a hydrophobic material, or by providing a hydrophobic coating onto one or more surfaces of the inner member 26. By providing the inner member 26 with a hydrophobic property, any body fluid coming into contact with the hydrophobic material of inner member skin interface member 20 will be repelled, preferably in a direction that leads it toward the inside of the housing 16, or it may be collected for performing an assay. According to a further optional construction, the skin penetration member (e.g., 34, FIG. 1) may be provided with a hydrophilic property, optionally via a hydrophilic coating applied thereto, which would attract body fluid in its vicinity. Providing the inner member with a hydrophobic property may also act to repel body fluid in close proximity thereto, thereby also having a possible effect of causing the body fluid to pool or form a well-defined drop on the surface of the skin. This effect, combined with the hydrophilic property of the skin penetration member can also promote the likelihood of efficient collection in transport of a sample of body fluid by the skin penetration member.

An additional optional feature of the arrangement 10 includes a cartridge 32. The cartridge 32 may include one or more components which are utilized to collect, transport, and perform an assay on a sample of body fluid, as will be described in more detail below. When the arrangement 10 includes such a cartridge 32, the skin interface member 20 may be provided with at least one contoured surface 33 which is intended to form a seal when pressed against the cartridge 32. The seal formed by the surface 33 against the cartridge 32 may optionally be substantially vacuum-tight. Thus, when vacuum is utilized as an optional catalyst, the seal formed by the surface 33 pressing against the cartridge 32 allows for the creation of a vacuum in the area of the skin 12 at the sampling site 14.

The arrangement 10 may further includes at least one skin penetration member 34. The at least one skin penetration member 34 can take any suitable form. For example, the at least one skin penetration member can comprise a solid lancet or a hollow needle. Conventional arrangements often require separate mechanisms for drawing a sample of blood to the surface of the skin and for transporting the sample to a reaction chamber. The arrangements of the present invention can optionally include a skin-piercing element in the form of a hollow needle to both create a wound opening and transport the sample, thereby greatly simplifying and improving the effectiveness of the arrangement 10.

According to one optional embodiment, the skin-penetration member(s) 34 can be in the form of a so-called "microneedle." As the name implies, microneedles are characterizable by their relatively small outer diameters. For example, a microneedle, as the term is utilized herein, may encompass a skin-penetration member having an outside diameter which is on the order of 40-200 μm. When the microneedle is hollow and comprises an inner lumen, the inside diameter can vary, for example, having an inside diameter on the order of 25-160 μm. Needles are also characterizable in the art by reference to the "gage." By way of illustration, and consistent with the above description, microneedles having a gage ranging from 26-36 are clearly comprehended by the present invention. Certain advantages may be gleaned from the use of such microneedles as the skin-penetration member. In particular, due to their small size, the size of the wound left upon entry into the skin is relatively small, thereby minimizing the pain associated with such needle insertions and allowing for a quicker healing process. However, the present invention is certainly not limited to the use of such microneedles. Thus, for example, according to one possible alternative embodiment, the skin penetration member(s) comprise hollow needles having a gage of about 20-25, or comprising hollow needles having an inner diameter of about 0.007 inches and an outer diameter of about 0.020 inches.

The at least one skin-penetration member 34 can be formed of any suitable material, such as metal, plastic, glass, etc. Optionally, the at least one skin penetration member can be in communication with an analyte quantification member 36. In further alternative embodiments, the analyte quantification member 36 may include an assay pad 38 comprising a reagent that changes color upon reaction with a target analyte, as known per se to those skilled in the art. The assay pad 38 is in fluid communication with the sample of body fluid. The assay pad 38 can be analyzed by a detector 42, such as an optical sensor, that forms part of the arrangement 10. Alternatively, the assay pad 38 can be removed from the arrangement 10 and inserted into a separate device, such as an electrochemical or photometric meter.

The at least one skin penetration member 34, and/or the analyte quantification member 36 may optionally be attached to an actuation element 40. The actuation element 40 can take any suitable form. For example, the actuation element 40 may comprise a mechanical, electrical or pneumatic element. According to the illustrated embodiment, the actuation element 40 is in the form of a mechanical spring. The actuation element 40 drives the at least one skin-penetration member 34 into the skin 12 at the sampling site 14, as indicated by the broken line outline of the skin-penetration member 34 as illustrated in FIG. 1.

As further illustrated in FIG. 1, the arrangement 10 can comprise a plurality of skin penetration members 34, analyte quantification members 36 and actuators 40 mounted within the cartridge 32. Thus, the arrangement 10, particularly when in the form of an integrated meter 11, is capable of performing a number of assays on collected body fluid samples in a fully self-contained manner. After a number of assays have been performed which correspond to the number of skin penetration members 34, analyte quantification members 36 and actuators 40, the cartridge 32 can be removed, discarded, and replaced with a new cartridge 32.

According to certain embodiments of the present invention, the arrangement 10, or integrated meter 11, can operate in an automatic or semi-automatic manner. For example, a user may place the skin interface member 20 over the surface of the skin 12 and when the user is ready to produce a sample of body fluid and/or perform an assay, the user initiates the process by, for example, pressing a button, touch screen, or other device interface (not shown). This can initiate a programmed sequence of events in the arrangement or integrated meter which may include one or more of actuation of a catalyst, and driving the skin-penetration member 34 into the skin. At a predetermined time, the catalyst device 14 is deactivated. This mode of operation can be characterized as "semi-automatic" in that sequence of events is manually initiated by the user.

According to one alternative, the mode of operation can be fully automatic. For example, the user places the skin interface member 20 over the skin 12 at a suitable sampling site. The arrangement 10, or integrated meter 11, can be provided with one or more sensors, such as sensors generically illustrated as element 31, that detect and verify that the skin interface member is properly located and ready for the sampling procedure to begin. Once this state has been sensed, the device automatically activates a programmed sequence of events in the device which may include one or more of activation of a catalyst, and driving the skin-penetration member 34 into the skin. At a subsequent predetermined time, the catalyst device 14 is deactivated. The catalyst device can be deactivated before, during or after the skin-piercing member is driven into the skin.

Figure 4:
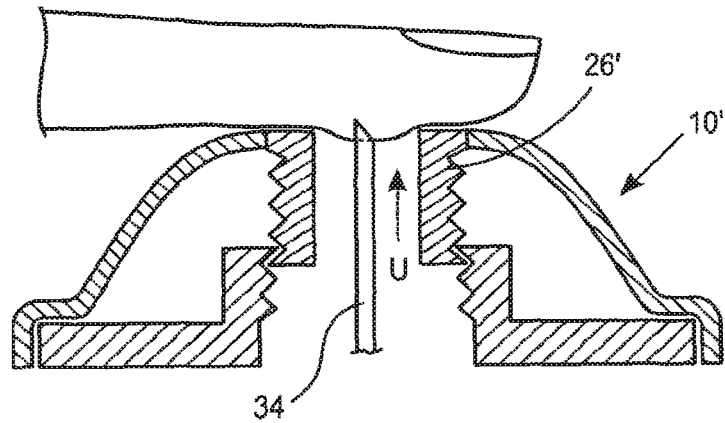
FIG. 4 is a partial sectional view of the arrangement of FIG. 3, shown in a first state.
Figure 5:
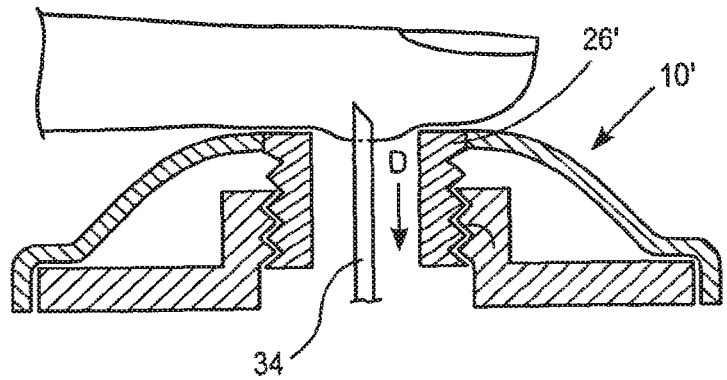
FIG. 5 is a partial sectional view of the arrangement of FIG. 3, shown in a second state.

The skin interface member 20 may be provided with a suitable construction so as to provide an adjustable mechanism for altering the above-mentioned separation distance between the housing and the surface of the skin. An illustrative example of one such arrangement 10' is contained in FIGS. 3-5. The arrangement 10' depicted in FIGS. 3-5 can be similar to the arrangement 10 previously described herein. According to the illustrative modified arrangement 10', the position of the skin interface member 20' relative to the housing 16' can be adjusted. Thus, for example, the housing 16' can be provided with an upwardly projecting flange 17 having a threaded inner surface 17a. The modified skin interface member 20' can be provided with an outer member 24' comprising an attachment 22' which is relatively movable with respect to the housing 16'. The modified skin interface member 20' may further include a relatively hard inner member 26' which is attached to the relatively softer outer member 24', and further includes a threaded outer surface 26a which mates with the threaded surface 17a of the housing 16'. Thus, by rotating the skin interface member 20' in a particular direction, the inner member 26', as well as the attached outer member 24' of the skin interface member 20' travels either up or down, as indicated by arrows U, D. As further illustrated in FIG. 4, travel in the direction of arrow U causes an increase in the separation distance SD, thereby reducing the penetration depth of a skin penetration member 34. Conversely, as illustrated in FIG. 5, travel in the direction of arrow D causes a reduction in the separation distance SD, thereby increasing the penetration depth of a skin penetration member 34. It should be understood that the arrangement 10' may include any of the features described in connection with any of the other embodiments described herein, including the arrangement 10 of FIGS. 1-2.

Figure 6:
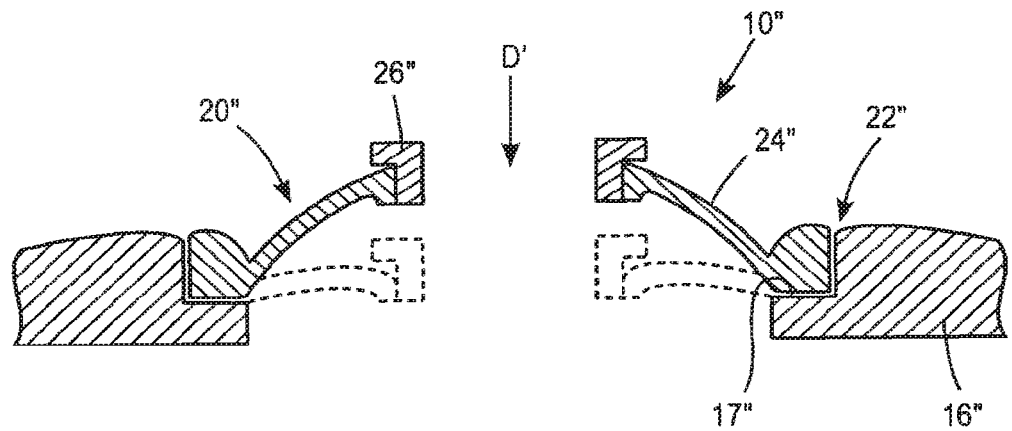
FIG. 6 is a partial sectional view of another arrangement formed according to an alternative embodiment of the present invention.

According to a further alternative construction of the present invention, a further modified arrangement 10" can be provided along the lines of the arrangement illustrated in FIG. 6. As illustrated therein, the arrangement 10" is constructed in a manner which is somewhat similar to the previously described arrangements 10, 10'. According to the arrangement 10" illustrated in FIG. 6, the skin interface member 20" is provided with a shape and/or configuration which buckles or provides a similar tactile sensation to the user upon pressing the skin interface member 20" in the direction of arrow D'. Thus, as illustrated, the skin interface member 20" can be provided with a relatively soft outer portion 24" that has a collapsible or flexible dome-like configuration. Thus, when the relatively hard inner member 26" is pressed in the direction of arrow D' the attached outer portion 24" flexes or deforms in the manner illustrated by the broken lines appearing in FIG. 4. This flexing or deformation produces a buckling sensation/sound, thereby providing tactile/audible feedback to the user with respect to an appropriate amount of force used to press on the relatively hard inner member 26". Upon removal of the downward force by the user, the skin interface member 20" has sufficient flexibility/resiliency to spring back to its initial position. The arrangement 10″ may further comprise a slightly modified housing 16″ and/or attachment 22″ construction. Thus, the housing 16″ may be provided with a shoulder 17″ upon which a portion of the outer member 24″ is seated, thereby forming an attachment 22″ between the skin interface member 20″ and the housing 16″. The attachment 22″ may be fixed or movable. It should be understood that the arrangement 10′ may include any of the features described in connection with any of the other embodiments described herein, including the arrangements 10, 10′ of FIGS. 1-5.

Additional alternative constructions for arrangements and/or skin interface members will now be described. However, it should be understood that any of the skin interface member embodiments described below can be utilized in conjunction with an arrangement including any combination of features of the arrangements described herein. The same reference numerals used above will also be used to describe corresponding features in the description of the following embodiments.

Figure 7:
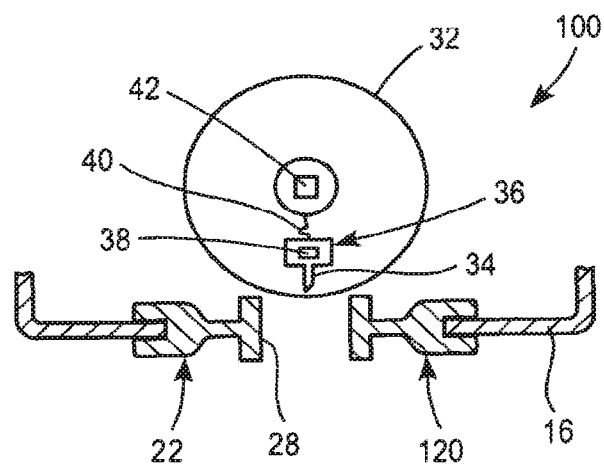
FIG. 7 is a partial cut away view of an arrangement formed according to a further alternative embodiment of the present invention.
Figure 8:
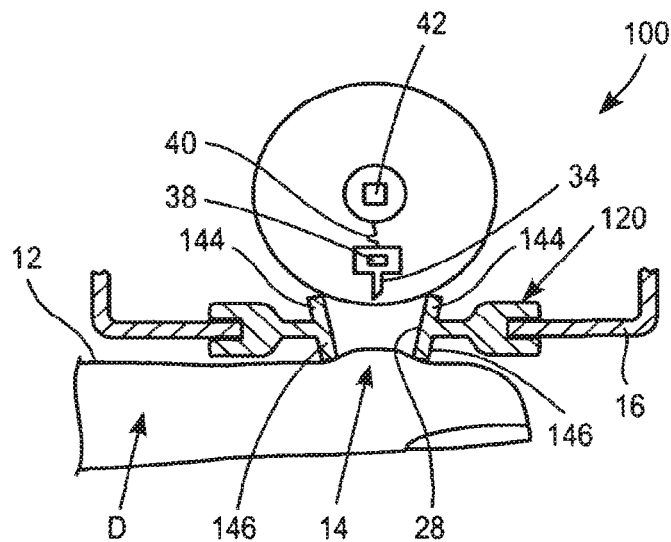
FIG. 8 is a partial cut away view of the arrangement of FIG. 7, after having been pressed against the skin of a user.

An alternative arrangement 100 constructed according to the principles of the present invention is illustrated in FIGS. 7-8. As illustrated therein, the arrangement 100 includes a modified skin interface member 120. The skin interface member 120 can be formed from any suitable material, such as an elastomer, silicone rubber, or plastic. The skin interface member 120 comprises a first projection 144 and a second projection 146. The first projection 144 is constructed and arranged to contact, and preferably form a seal against, the cartridge 32, as illustrated in FIG. 8. The seal formed against the cartridge 32 may be substantially vacuum-tight. The second projection 146 is constructed and arranged to contact the skin 12 of the user at the sampling site 14. As further illustrated in FIG. 8, the first and second projections 144, 146 are constructed and arranged such that upon being pressed against the skin 12, and optionally against the cartridge 32, the skin in the vicinity of the sampling site 14 is pinched due to a converging movement of the second projection 146. This convergence, or pinching movement, aids in the perfusion of body fluid at the sampling site 14, thereby improving the spontaneous production of a body fluid when the skin penetration member 34 is driven into the skin 12. Additional benefits of this embodiment include the potential for the above described pinching as creating a distraction to the user prior to insertion of the skin penetrating member into the skin, thereby diminishing the overall pain sensation of the body fluid sampling procedure.

Figure 9:
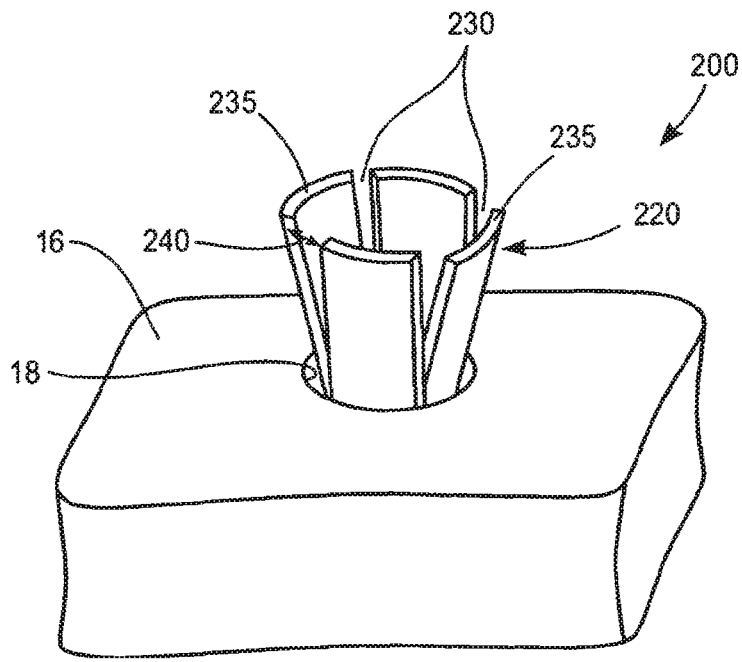
FIG. 9 is a partial perspective view of an alternative arrangement of the present invention.
Figure 10:
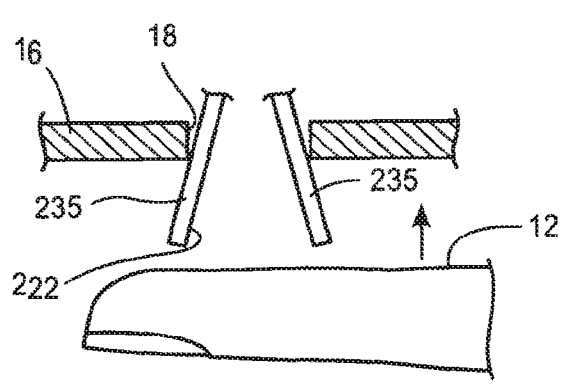
FIG. 10 is a partial side cut away view of the arrangement of FIG. 9.
Figure 11:
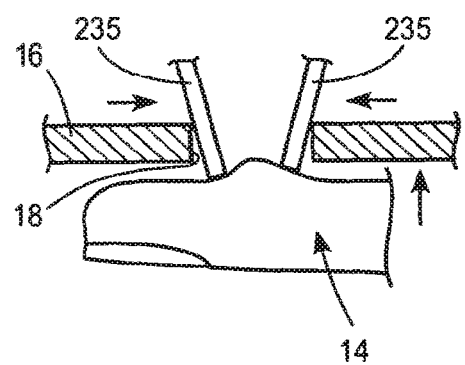
FIG. 11 is a partial side cut away view of the arrangement of FIG. 9, after having been pressed against the skin of the user.

An arrangement 200 formed according to a further alternative arrangement of the present invention is illustrated in FIGS. 9-11. The arrangement 200 includes a modified skin interface member 220 which is generally in the form of a tapered cylindrical member having an opening 222 constructed and arranged to be contacted by the skin 12 of the user. The skin interface member 220 comprises a plurality of longitudinal slits 230 thereby forming a plurality of longitudinal sections 235 which are separated from one another by a plurality of gaps 240. As illustrated, for example, in FIGS. 10-11, upon being pressed against the skin of the user the tapered cylindrical member 220 moves in a longitudinally downward direction within the first opening 18 of the housing 16. This longitudinally downward movement forces a plurality of longitudinal sections together in a converging manner so as to pinch the skin 12 of the user together at the sampling site 14. This convergence, or pinching movement, aids in the perfusion of body fluid at the sampling site 14, thereby improving the spontaneous production of a body fluid when the skin penetration member 34 is driven into the skin 12. Additional benefits of this construction include its simplicity of design and ease of manufacture, and the potential for the above described pinching as creating a distraction to the user prior to insertion of the skin penetrating member into the skin, thereby diminishing the overall pain sensation of the body fluid sampling procedure.

Figure 12:
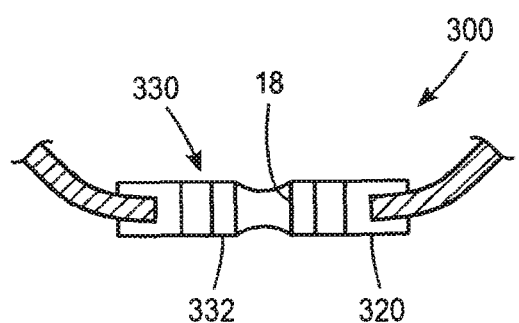
FIG. 12 is a partial cut away view of an arrangement formed according to yet another alternative embodiment of the present invention.
Figure 13:
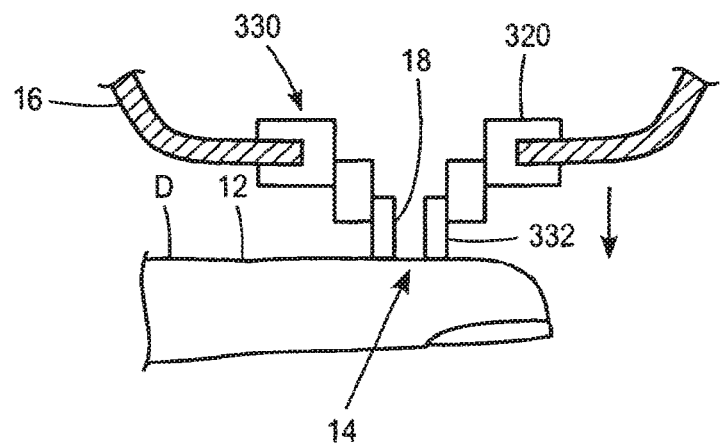
FIG. 13 is a partial cut away view of the arrangement of FIG. 12, after having been pressed against the skin of the user

FIGS. 12-13 illustrate yet another alternative arrangement 300 formed according to the principles of the present invention. As illustrated therein, the arrangement 300 includes a modified skin interface member 320. The skin interface member 320 comprises a plurality of concentric telescoping sections 330, including an innermost section 332 defining and opening 18 therein. Upon extension of the concentric telescoping sections 330, the innermost section 332 eventually engages the surface of the skin 12 of the user at the sampling site 14 in a manner which pinches the skin 12 in the vicinity of the sampling site 14. This convergence, or pinching movement, aids in the perfusion of body fluid at the sampling site 14, thereby improving the spontaneous production of a body fluid when the skin penetration member 34 is driven into the skin 12. Additional benefits of this construction include the ability to store the skin interface member 320 with a low profile when not in use, and the potential for the above described pinching as creating a distraction to the user prior to insertion of the skin penetrating member into the skin, thereby diminishing the overall pain sensation of the body fluid sampling procedure.

Figure 14:
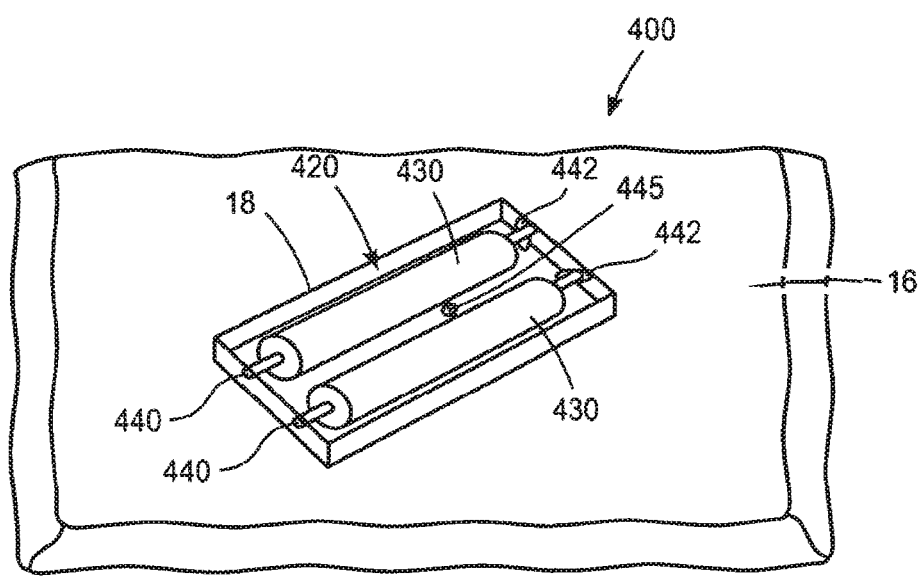
FIG. 14 is a perspective view of an arrangement of a further embodiment of the present invention.
Figure 15:
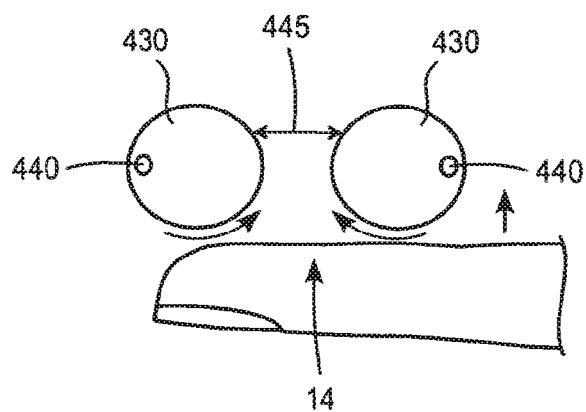
FIG. 15 is a partial side view of the arrangement of FIG. 14.
Figure 16:
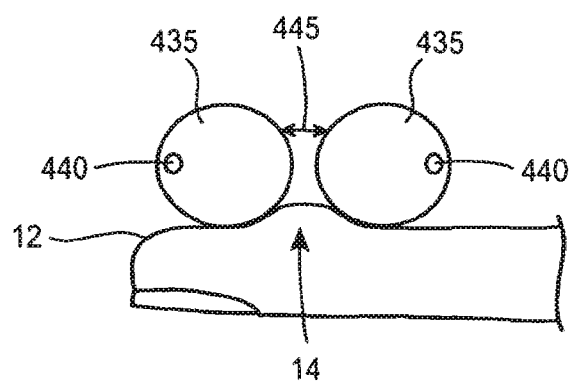
FIG. 16 is a partial side view of the arrangement of FIG. 14, after having been pressed against the skin of the user.

Yet another arrangement 400 formed according to the principles of the present invention is illustrated in FIGS. 14-16. The arrangement 400 includes a modified skin interface member 420 disposed within an opening 18 of the housing 16. As illustrated therein, the skin interface member 420 comprises a plurality of rolling members 430 connected to pivots or axles 440 disposed in at least both longitudinal ends of each rolling member 430. The pivots or axles 440 are mounted in corresponding bores 442. As illustrated in FIGS. 15-16, upon pressing against the skin 12 of the user a gap 445 defined between the rolling members 430 is caused to converge. This can be accomplished by a number of different mechanisms. For example, as illustrated in FIG. 14, the pivots or axles 440 can be mounted within bores 442 which are angled toward one another. Alternatively, the bores 442 can be substantially circular, and the pivots or axles 440 can be offset with respect to the longitudinal center axis of the rolling elements (FIGS. 15-16) so as to produce the desired convergence or closing of the gap 445. This convergence of the rolling elements 430 pinches the skin 12 of the user in the vicinity of sampling site 14. Additional and benefits of this embodiment include its simplicity and ease of manufacture, and the potential for the above described pinching as creating a distraction to the user prior to insertion of the skin penetrating member into the skin, thereby diminishing the overall pain sensation of the body fluid sampling procedure.

Figure 17:
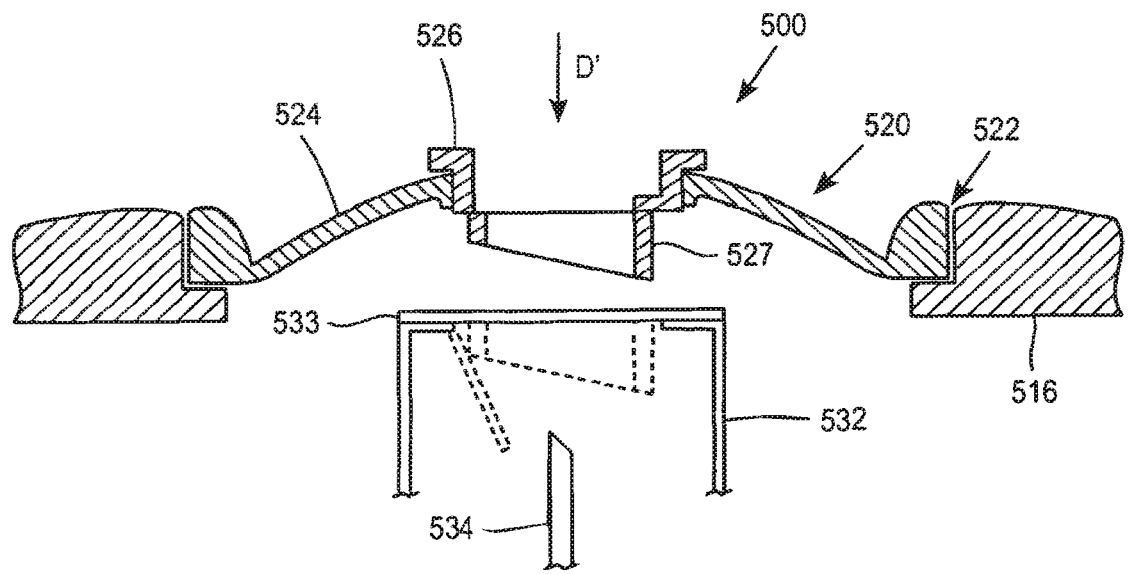
FIG. 17 is a sectional view of an arrangement formed according to another aspect of the present invention.
Figure 18:
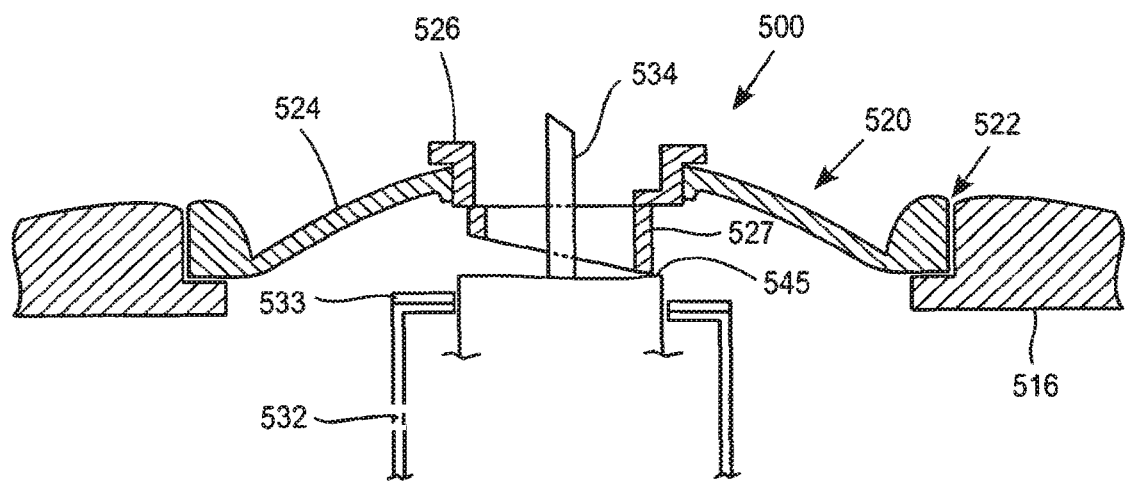
FIG. 18 is a sectional view of the arrangement of FIG. 17, shown in a different state.

FIGS. 17-18 illustrates arrangements formed according to other alternative embodiments of the present invention. As illustrated therein, the arrangement 500 may include a housing 516 constructed in a manner which is similar to that previously described herein. A modified skin interface member 520 is connected to the housing 516 via a suitable attachment 522. According to this embodiment, the skin interface member 520 is provided with a suitable punch or cutting mechanism. Thus, according to the non-limiting illustrated example, the skin interface member 520 is provided with a relatively hard inner member 526 and a downwardly projecting member 527 which including a formation or shape for facilitating a cutting or punching action, such as sharpened lower corner. The inner member 525 and the downwardly projecting member 527 may be integral with or removably connected to a relatively softer flexible outer member 524, as described at length herein. The arrangement 500 is useful when used in connection with a frangible component. Thus, for example, the arrangement 500 may optionally include a cartridge 532, which may have one or more of the features described in connection with the cartridge 32 of previous embodiments. The cartridge 532 may include a frangible component 533. The frangible component 533 may take the form of a seal, such as a thin layer of foil or similar material which provides a sealed protected environment inside of the cartridge 532. As previously explained herein, the cartridge 532 may include one or more skin penetration member(s) 534. Prior to, or concurrently with, actuation of the skin penetration member 534 to pierce the skin, the skin interface member 520 may be urged in the direction of arrow D' thereby creating an opening in the frangible component 533, as illustrated in the broken line portion of FIG. 17. The skin penetration member 534 is now free to travel through the opening created by the skin interface member 520 in the frangible component 533, and eventually into the surface of the skin at the sampling site. According to a further optional aspect, the downwardly projecting member 527 may also serve as a stop to limit the depth of penetration of the skin penetration member 534, as illustrated in FIG. 18. As illustrated therein, the skin penetration member 534 may be provided with a suitable stopping mechanism, such as the illustrated shoulder or collar 545. Regardless of the specific form of the stopping member, it shall be provided with a construction such that the stopping member 545 passes through the opening in the cartridge 532, but does not pass through the opening presented by the bottom of the downwardly projecting member 527. It should be understood that the skin interface member 520 may be provided with a number of alternative constructions, not specifically illustrated, which may provide the above described punching or cutting or punching action.

Figure 19:
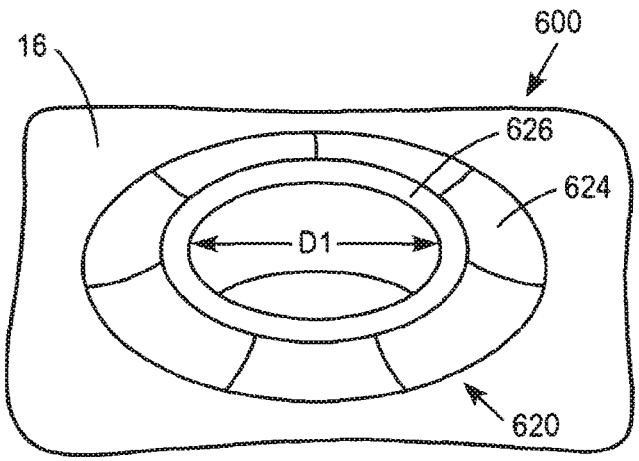
FIG. 19 is a partial perspective view of an arrangement formed according to an additional embodiment of the present invention, in a first state.
Figure 20:
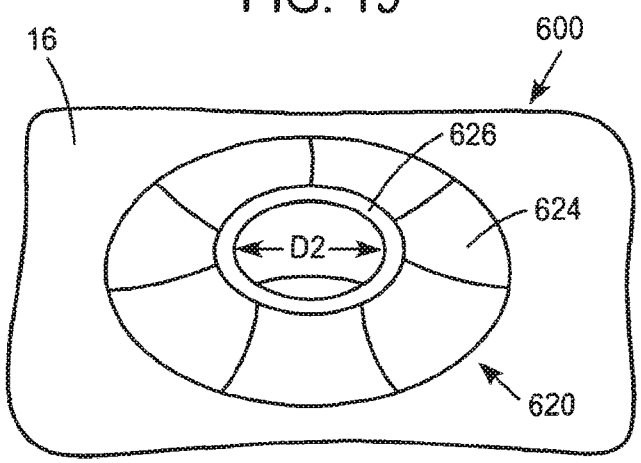
FIG. 20 is a partial perspective of the arrangement of FIG. 19, in a second state.
Figure 21:
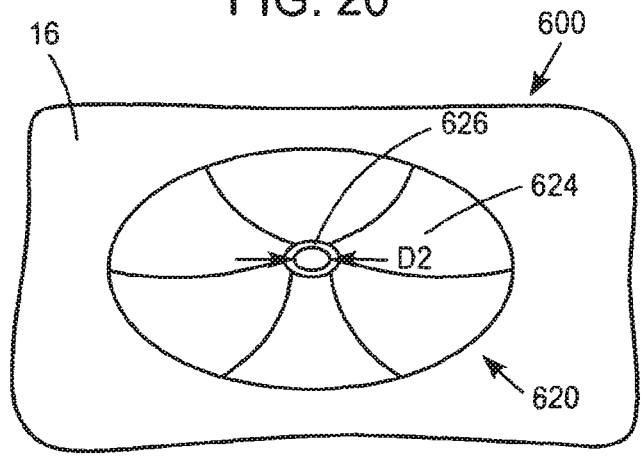
FIG. 21 is a partial perspective of the arrangement of FIG. 19, in a third state.

FIGS. 19-21 illustrate embodiments whereby the size of the opening of the inner member of the skin interface member can be changed. The ability to change the size of the opening can provide certain benefits and advantages For example, varying the opening size can act as a catalyst by producing a squeezing of pulsing pressure on the skin at the sampling site, and/or by controlling the distance that the skin can stretch into the opening of the inner member, thereby providing a depth control mechanism. Also, the ability to close, or substantially close, the opening in the skin interface member can provide the ability to act as a shutter to shut out or limit exposure to the external environment and/or ambient light. An arrangement 600 is illustrated in FIGS. 19-21 is a non-limiting example of a specific construction for achieving the above-noted objectives. As illustrated therein, the arrangement 600 includes a skin interface member 620 connected to a housing 16 by any suitable manner, such as those previously described herein. The skin interface member comprises a relatively soft and flexible outer member 624 attached to a relatively hard inner member 626. The inner member 626 is provided with a nominal opening having a first diameter D1, and any suitable mechanism or construction for changing the diameter of the opening to a second smaller diameter D2. According to one nonlimiting example, the inner member 626 can be formed, at least in part, from a shape memory material. Thus, upon application of an appropriate stimulus, the material changes shape in a manner such that the diameter of the opening is reduced. Any suitable shape memory material can be utilized for this purpose. For example, the inner member 626 may be formed from a shape memory metal, such as Nitinol™. Exemplary stimuli include heat or electrical current. This reduction in diameter of the opening of the inner member 626 can be utilized to produce one or more of the following effects: squeezing of the skin at the sampling site which is present within the nominal opening diameter D1, reducing the amount of skin which can protrude down into the opening of the inner member 626, thereby reducing the depth of penetration of a skin penetration member at the sampling site; and act as a shutter to shut out or limit exposure to the external environment and/or ambient light (FIG. 21).

The stimulus or mechanism for effecting the change in diameter can be initiated manually by a user, or automatically by an associated device. For example, a user can select an appropriate interface mechanism to initiate a single reduction in diameter, or to initiate a cycle of changes in diameter between a larger diameter opening (D1) and a smaller diameter opening (D2). Alternatively, the stimulus or mechanism for effecting change in diameter can be automatically initiated by an associated device such as an arrangement or integrated meter as described herein. For example, the device may be provided with one or more sensors, such as those previously described herein, which are capable of sensing contact of the device with the surface of the skin of a user, and/or a pressure associated therewith. According to one alternative embodiment, if the device fails to detect contact with the skin, an appropriate stimulus, such as an electrical current, can be automatically generated by the device and applied to a shape memory material forming the inner member 626 thereby causing an appropriate reduction in diameter. Thus, the device may automatically enter a shutdown or standby mode wherein the diameter (D2) of the opening of the inner member 626 is reduced to such an extent that it entirely closes, or substantially closes, the opening in the inner member 626, thereby shielding the inside of the device from the external environment and/or ambient light (e.g., FIG. 21). According to a further alternative embodiment, the size or diameter of the opening in the inner member 626 can be changed automatically based on the results of previous sample collection efforts. For example, an arrangement can be provided with sensors that detect the presence of a body fluid, such as blood, as it enters the device. Sensors can also be provided that measure or estimate the volume of body fluid, e.g., blood. Conventional sensors can be used for this purpose. If the arrangement senses a lack of body fluid, or an inadequate volume of body fluid, a signal or stimulus can be sent to the inner member to increase the diameter of the opening in the inner member 626. This larger opening permits a deeper projection of the skin surface into the larger opening thereby allowing a deeper penetration by a skin penetration member, leading to a greater probability of obtaining adequate sample size. Of course, the arrangement can operate in the opposite manner; namely, upon sensing an oversupply of body fluid a signal or stimulus can be sent to trigger a reduction in the diameter of the opening in the inner member 626, thereby having the opposite effect on penetration depth as an increase in the diameter thereof.

As noted above, a number of alternative mechanisms are contemplated for providing the desired change in diameter of the inner member of the skin interface member 620. One such alternative is illustrated in FIGS. 22-23. As illustrated therein, the inner member 627' is in the form of a collapsible annular member formed from relatively movable segments 627'a. A suitable actuator 629, such as a cam mechanism/lever can be utilized to cause movement of the segments 627'a relative to one another thereby causing the above described reduction in diameter from D1 (FIG. 22) to D2 (FIG. 23) by movement of the actuator 629 initiated manually by the user or automatically by an associated device.

Another alternative mechanism is illustrated in FIG. 24. As illustrated therein, the inner member 627″ can be provided with a keyhole-like configuration. The keyhole-like configuration is composed of a first portion 631 having a relatively large diameter opening D1 and a second portion 633 having a relatively small diameter opening D2. Thus, the desired reduction in diameter effect is realized by placing the skin over the first portion 631, then moving the skin in the direction of the second portion 633, or in the direction of arrow DR.

Figure 25:
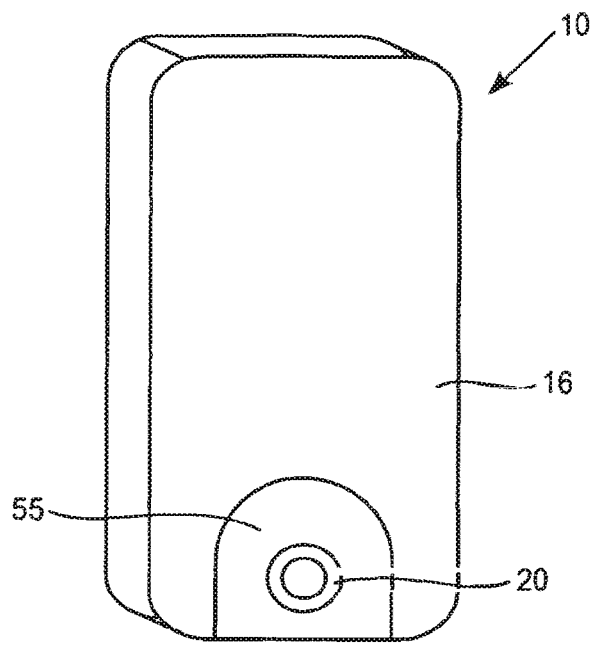
FIG. 25 is a perspective view of an arrangement formed according to a further alternative embodiment of the present invention.
Figure 26:
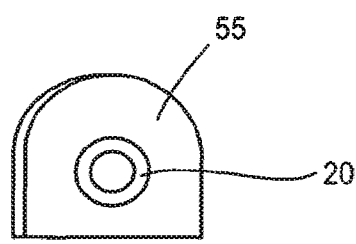
FIG. 26 is a perspective view of a portion of the arrangement of FIG. 25.

FIGS. 25-26 illustrates an additional alternative embodiment according to the principles of the present invention. According to this aspect of the present invention, the skin interface member 20 can be attached or otherwise associated with a plate-like member 55. The plate-like member 55 is in turn removably mounted to or associated with a housing 16 of a device or arrangement 10. The skin interface member 20 can either be permanently affixed or associated with the plate-like member 55, or can be removably mounted thereto. The plate-like member 55 can be associated with a housing 16 by any suitable mechanism, such as frictional interface, detents, snaps, fasteners, adhesives, and the like. Preferably, the plate-like member 55 is removable from the remaining portion of the housing 16, so that a new or different plate-like member 55 containing a new or different skin interface member 20 can be used to replace an existing plate-like member 55/interface member 20. This arrangement is beneficial in that, after a period of use, the skin interface member 20 and/or the plate 55 may become contaminated with body fluids, such as blood. Therefore, it is desirable to be able to exchange this portion of an arrangement 10 with a fresh skin interface member 20/plate-like member 55 unit. In addition, this type of arrangement also improves flexibility in terms of providing a mechanism for introducing different types of skin interface members 20. For example, if a user is having difficulty obtaining an adequate sample of blood using a certain skin interface member 20 configuration, the user can select a different interface member 20 which may provide for better blood acquisition. It should be understood that the arrangement 10 can have any suitable configuration and/or combination of features, such as those previously described herein. Similarly, the skin interface member 20 can be configured in any suitable manner. Therefore, the skin interface member 20 may have any of the configurations and/or features of the previously described embodiments. The plate-like member 55 can be formed from any suitable material, such as plastic or metal, and can be of any suitable configuration or geometry.

An exemplary body fluid sampling method or technique which may be used in conjunction with any of the above-described arrangements, but is not necessarily limited thereto, is described as follows.

A skin interface member is placed on the skin over a sampling site located on a digit or at an alternate site. The skin interface member has an opening therein which corresponds to the sampling site. The skin interface member is provided with a construction that aids or facilitates the perfusion of blood at the sampling site, such as any of the skin interface member constructions described herein, in order to improve the probability of a spontaneous expression of blood upon wound creation. A sequence of events is then initiated. The events can be initiated manually, for example, by pressing a button or other triggering mechanism. Alternatively, the events can be automatically triggered, for example, through the use of one or more sensors which determine when the skin interface member has been properly positioned over a sampling site on the surface of the skin. A catalyst is then optionally applied to the sampling site. The catalyst can comprise one or more of heat, pressure, vacuum, vibration, topical drugs, squeezing or combinations thereof. These catalysts can be applied concurrently or sequentially relative to one another. According to one embodiment, a catalyst in the form of vacuum pressure is applied to the sampling site via a suitable mechanism, such as a pump capable of creating vacuum pressure. The catalyst can be applied for a set period of time, and then removed or terminated. For example, the catalyst can be removed before, during, or after penetration of the skin. Next, at least one skin penetration member is actuated or driven into the surface of the skin. The skin penetration member can take any suitable form, such as a solid lancet or hollow needle (e.g., a microneedle). According to one embodiment, the at least one skin penetration member comprises a hollow needle having a first end configured to pierce the surface of the skin, and an inner lumen. The at least one skin penetration member can be actuated via any suitable mechanism, such as a mechanical spring. According to one embodiment, body fluid is transported away from the wound site via a suitable mechanism. According to one embodiment, the body fluid, or blood, is transported via the inner lumen of a hollow skin-penetration member via capillary action, vacuum, or a combination of both. The body fluid can be transported to an analyte quantification member of any suitable construction. According to one embodiment, the analyte quantification member comprises an assay pad which contains a chemical reagent impregnated therein. Upon exposure to the body fluid, a target analyte contained therein causes a chemical reaction with the reagent producing a color change in the assay pad. This color change can in turn be detected by a suitable detection element. One such detection element comprises an optical sensor.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. § 112, ¶6, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. An arrangement for producing a sample of body fluid from a wound opening created in a skin surface at a sampling site, the arrangement comprising:
   a housing comprising a first opening;
   a first skin interface member disposed in the first opening and removably attached thereto, the first skin interface member comprising a second opening;
   a second skin interface member configured to be disposed in the first opening and removably attached thereto; and at least one skin-penetration member comprising a penetrating end aligned with the second opening;

wherein the first skin interface member is exchangeable with the second skin interface member, the first skin interface member configured to provide a first penetration depth of the skin-penetration member into the skin surface, and the second skin interface member configured to provide a second penetration depth of the skin-penetration member into the skin surface.

2. The arrangement of claim 1, wherein the first skin interface member differs in at least one dimension compared to the second skin interface member.

3. The arrangement of claim 2, wherein the first skin interface member has a first thickness and the second skin interface member has a second thickness different from the first thickness.

4. The arrangement of claim 1, wherein the second opening has a variable diameter.

5. The arrangement of claim 1, wherein the first skin interface member comprises an inner member comprising the second opening and an outer member at least partially surrounding the inner member, wherein a perimeter portion of the outer member is affixed to the housing.

6. The arrangement of claim 5, wherein the inner member and the outer member are integral.

7. The arrangement of claim 5, wherein the outer member is configured to flex more than the inner member upon application of force to the first skin interface member.

8. The arrangement of claim 1, further comprising a cartridge disposed within the housing, wherein the at least one skin-penetration member is disposed within the cartridge.

9. The arrangement of claim 8, wherein the cartridge further comprises at least one analyte quantification member.

10. The arrangement of claim 9, wherein the analyte quantification member comprises an assay pad containing a chemical reagent.

11. The arrangement of claim 8, wherein the cartridge comprises an outer surface, and wherein the first skin interface member is constructed and arranged to form a seal with the outer surface of the cartridge upon being pressed against the skin of the user.

12. The arrangement of claim 8, further comprising a plurality of skin-penetration members and a plurality of analyte quantification members operatively arranged in the cartridge such that multiple tests can be performed using the arrangement without replacing the cartridge.

13. The arrangement of claim 1, further comprising at least one sensor capable of detecting when the first skin interface member contacts the skin surface of a user at the sampling site.

14. The arrangement of claim 1, wherein the first skin interface member is coupled to a first housing member and the second skin interface member is coupled to a second housing member, the first skin interface member is removeably attached to the housing via the first housing member, the second skin interface member is configured to be removeably attached to the first opening via the second housing member, and the first housing member is exchangeable with the second housing member.

15. The arrangement of claim 14, wherein the first and second housing members each comprise a plate.

16. The arrangement of claim 14, wherein the first skin interface member differs in at least one dimension compared to the second skin interface member.

17. The arrangement of claim 16, wherein the first skin interface member has a first thickness and the second skin interface member has a second thickness different from the first thickness.

18. The arrangement of claim 14, wherein the first skin interface member comprises an inner member comprising the second opening and an outer member at least partially surrounding the inner member, wherein a perimeter portion of the outer member is affixed to the first housing member.

19. The arrangement of claim 18, wherein the inner member and the outer member are integral.

20. The arrangement of claim 18, wherein the outer member is configured to flex more than the inner member upon application of force to the first skin interface member.

21. The arrangement of claim 14, further comprising a cartridge disposed within the housing, wherein the at least one skin-penetration member is disposed within the cartridge.

22. The arrangement of claim 21, wherein the cartridge further comprises at least one analyte quantification member.

23. The arrangement of claim 22, wherein the analyte quantification member comprises an assay pad containing a chemical reagent.

24. The arrangement of claim 22, wherein the cartridge comprises an outer surface, and wherein the first skin interface member is constructed and arranged to form a seal with the outer surface of the cartridge upon being pressed against the skin of the user.

25. The arrangement of claim 22, further comprising a plurality of skin-penetration members and a plurality of analyte quantification members operatively arranged in the cartridge such that multiple tests can be performed using the arrangement without replacing the cartridge.

* * * * *